(12) United States Patent
Gray et al.

(10) Patent No.: US 12,396,867 B2
(45) Date of Patent: Aug. 26, 2025

(54) EXPANDABLE FOOTPRINT IMPLANT

(71) Applicant: GLOBUS MEDICAL, INC., Audubon, PA (US)

(72) Inventors: Jason Gray, East Greenville, PA (US); David Feigenbaum, Philadelphia, PA (US)

(73) Assignee: Globus Medical, Inc., Audubon, PA (US)

( * ) Notice: Subject to any disclaimer, the term of this patent is extended or adjusted under 35 U.S.C. 154(b) by 345 days.

(21) Appl. No.: 18/187,107

(22) Filed: Mar. 21, 2023

(65) Prior Publication Data
US 2024/0315851 A1     Sep. 26, 2024

Related U.S. Application Data

(63) Continuation of application No. 18/124,095, filed on Mar. 21, 2023.

(51) Int. Cl.
*A61F 2/44* (2006.01)
*A61F 2/30* (2006.01)
*A61F 2/46* (2006.01)

(52) U.S. Cl.
CPC .......... *A61F 2/447* (2013.01); *A61F 2/4455* (2013.01); *A61F 2002/30537* (2013.01); *A61F 2002/3055* (2013.01); *A61F 2002/30556* (2013.01); *A61F 2002/30579* (2013.01); *A61F 2002/449* (2013.01); *A61F 2002/4627* (2013.01)

(58) Field of Classification Search
CPC .......... A61F 2/447; A61F 2/44; A61F 2/4461; A61F 2002/30537; A61F 2002/3055; A61F 2002/30556; A61F 2002/30579; A61F 2002/449; A61F 2002/4627
USPC .......................................... 623/17.11–17.16
See application file for complete search history.

(56) References Cited

U.S. PATENT DOCUMENTS

| | | | |
|---|---|---|---|
| 4,349,921 A | 9/1982 | Kuntz |
| 4,599,086 A | 7/1986 | Doty |
| 4,863,476 A | 9/1989 | Shepperd |
| 4,863,477 A | 9/1989 | Monson |
| 5,123,926 A | 6/1992 | Pisharodi |
| 5,290,312 A | 3/1994 | Kojimoto et al. |
| 5,306,310 A | 4/1994 | Siebels |
| 5,375,823 A | 12/1994 | Navas |
| 5,390,683 A | 2/1995 | Pisharodi |
| 5,522,899 A | 6/1996 | Michelson |
| 5,534,030 A | 7/1996 | Navarro et al. |

(Continued)

FOREIGN PATENT DOCUMENTS

| | | |
|---|---|---|
| CA | 2088066 A1 | 1/1992 |
| DE | 4012622 C1 | 7/1991 |

(Continued)

*Primary Examiner* — Jessica Weiss

(57) ABSTRACT

Expandable intervertebral fusion implants, system, and methods. The expandable intervertebral implant is capable of being installed inside an intervertebral disc space to maintain disc spacing and restore spinal stability, thereby facilitating an intervertebral fusion. The implant may include a central drive assembly configured to control left and right side assemblies. The expandable intervertebral implant may be configured to transition from a collapsed configuration having a first width and a first height to an expanded configuration having a second width and a second height.

18 Claims, 13 Drawing Sheets

(56) References Cited

U.S. PATENT DOCUMENTS

| | | |
|---|---|---|
| 5,554,191 A | 9/1996 | Lahille et al. |
| 5,571,192 A | 11/1996 | Schonhoffer |
| 5,645,596 A | 7/1997 | Kim |
| 5,653,763 A | 8/1997 | Errico et al. |
| 5,665,122 A | 9/1997 | Kambin |
| 5,676,701 A | 10/1997 | Yuan et al. |
| 6,039,761 A | 3/2000 | Li et al. |
| 6,045,579 A | 4/2000 | Hochschuler et al. |
| 6,080,193 A | 6/2000 | Hochschuler et al. |
| 6,099,531 A | 8/2000 | Bonutti |
| 6,126,689 A | 10/2000 | Brett |
| 6,176,882 B1 | 1/2001 | Biedermann et al. |
| 6,258,125 B1 | 7/2001 | Paul et al. |
| 6,554,863 B2 | 4/2003 | Paul et al. |
| 6,558,423 B1 | 5/2003 | Michelson |
| 6,562,074 B2 | 5/2003 | Gerbec et al. |
| 6,576,016 B1 | 6/2003 | Hochschuler et al. |
| 6,641,614 B1 | 11/2003 | Wagner et al. |
| 6,648,917 B2 | 11/2003 | Gerbec et al. |
| 6,666,891 B2 | 12/2003 | Boehm, Jr. et al. |
| 6,692,495 B1 | 2/2004 | Zacouto |
| 6,706,070 B1 | 3/2004 | Wagner et al. |
| 6,752,832 B2 | 6/2004 | Ulrich |
| 6,814,756 B1 | 11/2004 | Michelson |
| 6,830,589 B2 | 12/2004 | Erickson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,881,228 B2 | 4/2005 | Zdeblick et al. |
| 7,018,415 B1 | 3/2006 | McKay |
| 7,070,598 B2 | 7/2006 | Lim et al. |
| 7,204,853 B2 | 4/2007 | Gordon |
| 7,217,291 B2 | 5/2007 | Zucherman et al. |
| 7,282,063 B2 | 10/2007 | Cohen et al. |
| 7,316,714 B2 | 1/2008 | Gordon |
| 7,473,276 B2 | 1/2009 | Aebi et al. |
| 7,547,325 B2 | 6/2009 | Biedermann et al. |
| 7,621,953 B2 | 11/2009 | Braddock, Jr. et al. |
| 7,641,693 B2 | 1/2010 | Gutlin et al. |
| 7,682,396 B2 | 3/2010 | Beaurain et al. |
| 7,749,270 B2 | 7/2010 | Peterman |
| 7,753,958 B2 | 7/2010 | Gordon |
| 7,771,473 B2 | 8/2010 | Thramann |
| 7,780,732 B2 | 8/2010 | Abernathie |
| 7,799,081 B2 | 9/2010 | McKinley |
| 7,815,683 B2 | 10/2010 | Melkent et al. |
| 7,837,734 B2 | 11/2010 | Zucherman et al. |
| 7,875,078 B2 | 1/2011 | Wysocki et al. |
| 7,901,409 B2 | 3/2011 | Canaveral et al. |
| 7,909,869 B2 | 3/2011 | Gordon |
| 7,951,199 B2 | 5/2011 | Miller |
| 7,985,256 B2 | 7/2011 | Grotz et al. |
| 8,062,375 B2 | 11/2011 | Glerum |
| 8,070,813 B2 | 12/2011 | Grotz et al. |
| 8,123,810 B2 | 2/2012 | Gordon |
| 8,137,405 B2 | 3/2012 | Kostuik et al. |
| 8,192,495 B2 | 6/2012 | Simpson et al. |
| 8,303,663 B2 | 11/2012 | Jimenez et al. |
| 8,377,140 B2 | 2/2013 | DeFalco et al. |
| 8,394,129 B2 | 3/2013 | Lopez et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,647,386 B2 | 2/2014 | Gordon |
| 8,696,751 B2 | 4/2014 | Ashley et al. |
| 8,771,360 B2 | 7/2014 | Jimenez et al. |
| 8,894,710 B2 | 11/2014 | Simpson et al. |
| 8,932,355 B2 | 1/2015 | Grotz et al. |
| 8,940,049 B1 | 1/2015 | Jimenez et al. |
| 8,956,413 B2 | 2/2015 | Ashley et al. |
| 8,992,620 B2 | 3/2015 | Ashley et al. |
| 9,028,550 B2 | 5/2015 | Shulock et al. |
| 9,358,125 B2 | 6/2016 | Jimenez et al. |
| 9,532,883 B2 | 1/2017 | McLuen et al. |
| 9,622,878 B2 | 4/2017 | Grotz |
| 11,166,826 B2 * | 11/2021 | Huang .................... A61F 2/447 |
| 11,224,522 B2 * | 1/2022 | To ........................ A61F 2/4455 |
| 11,253,376 B2 * | 2/2022 | To ........................ A61F 2/4611 |
| 11,285,018 B2 | 3/2022 | Shoshtaev |
| 11,357,640 B2 | 6/2022 | Weiman et al. |
| 11,684,484 B2 * | 6/2023 | Shoshtaev ............. A61F 2/4425 |
| | | 623/17.16 |
| 2002/0045945 A1 | 4/2002 | Liu |
| 2002/0068976 A1 | 6/2002 | Jackson |
| 2002/0068977 A1 | 6/2002 | Jackson |
| 2003/0176926 A1 | 9/2003 | Boehm et al. |
| 2004/0030387 A1 | 2/2004 | Landry et al. |
| 2004/0049271 A1 | 3/2004 | Biedermann |
| 2004/0054412 A1 | 3/2004 | Gerbec et al. |
| 2004/0087947 A1 | 5/2004 | Lim et al. |
| 2004/0153065 A1 | 8/2004 | Lim |
| 2005/0021041 A1 | 1/2005 | Michelson |
| 2005/0021145 A1 | 1/2005 | de Villiers et al. |
| 2005/0033432 A1 | 2/2005 | Gordon |
| 2005/0080422 A1 | 4/2005 | Otte et al. |
| 2005/0113916 A1 | 5/2005 | Branch |
| 2005/0149188 A1 | 7/2005 | Cook |
| 2005/0171541 A1 | 8/2005 | Boehm |
| 2005/0251258 A1 | 11/2005 | Jackson |
| 2005/0273171 A1 | 12/2005 | Gordon |
| 2005/0273174 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0004453 A1 | 1/2006 | Bartish et al. |
| 2006/0015184 A1 | 1/2006 | Winterbottom et al. |
| 2006/0058878 A1 | 3/2006 | Michelson |
| 2006/0084986 A1 | 4/2006 | Grinberg et al. |
| 2006/0122701 A1 | 6/2006 | Kister |
| 2006/0129244 A1 | 6/2006 | Ensign |
| 2006/0142859 A1 | 6/2006 | Mcluen |
| 2006/0149385 A1 | 7/2006 | Mckay |
| 2006/0195192 A1 | 8/2006 | Gordon et al. |
| 2006/0229729 A1 | 10/2006 | Gordon |
| 2006/0241770 A1 | 10/2006 | Rhoda et al. |
| 2006/0253201 A1 | 11/2006 | Mcluen |
| 2007/0043442 A1 | 2/2007 | Abernathie |
| 2007/0050030 A1 | 3/2007 | Kim |
| 2007/0050032 A1 | 3/2007 | Gittings et al. |
| 2007/0055377 A1 | 3/2007 | Hanson et al. |
| 2007/0191951 A1 | 8/2007 | Branch |
| 2007/0255415 A1 | 11/2007 | Edie et al. |
| 2007/0270963 A1 | 11/2007 | Melkent et al. |
| 2007/0270968 A1 | 11/2007 | Baynham |
| 2008/0021559 A1 | 1/2008 | Thramann |
| 2008/0065222 A1 | 3/2008 | Hamada |
| 2008/0114467 A1 | 5/2008 | Capote et al. |
| 2008/0140207 A1 | 6/2008 | Olmos et al. |
| 2008/0147194 A1 | 6/2008 | Grotz et al. |
| 2008/0161933 A1 | 7/2008 | Grotz et al. |
| 2008/0167657 A1 | 7/2008 | Greenhalgh |
| 2008/0183204 A1 | 7/2008 | Greenhalgh et al. |
| 2008/0221694 A1 | 9/2008 | Warnick et al. |
| 2008/0275455 A1 | 11/2008 | Berry et al. |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0306488 A1 | 12/2008 | Altarac et al. |
| 2008/0319487 A1 | 12/2008 | Fielding et al. |
| 2008/0319549 A1 | 12/2008 | Greenhalgh et al. |
| 2009/0024217 A1 | 1/2009 | Levy et al. |
| 2009/0062833 A1 | 3/2009 | Song |
| 2009/0076616 A1 | 3/2009 | Duggal et al. |
| 2009/0125062 A1 | 5/2009 | Amin |
| 2009/0149956 A1 | 6/2009 | Greenhalgh et al. |
| 2009/0149959 A1 | 6/2009 | Conner et al. |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 | 12/2009 | McCormack |

(56) References Cited

U.S. PATENT DOCUMENTS

| | | |
|---|---|---|
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0145455 A1 | 6/2010 | Simpson et al. |
| 2010/0179657 A1 | 7/2010 | Greenhalgh et al. |
| 2010/0211176 A1 | 8/2010 | Greenhalgh |
| 2010/0222816 A1 | 9/2010 | Gabelberger et al. |
| 2010/0286783 A1 | 11/2010 | Lechmann et al. |
| 2011/0035011 A1 | 2/2011 | Cain |
| 2011/0093074 A1 | 4/2011 | Glerum et al. |
| 2011/0160861 A1 | 6/2011 | Jimenez et al. |
| 2011/0172774 A1 | 7/2011 | Varela |
| 2011/0276142 A1 | 11/2011 | Niemiec et al. |
| 2011/0301713 A1 | 12/2011 | Theofilos |
| 2011/0319997 A1 | 12/2011 | Glerum et al. |
| 2012/0035729 A1 | 2/2012 | Glerum et al. |
| 2012/0059470 A1 | 3/2012 | Weiman |
| 2012/0059472 A1 | 3/2012 | Weiman |
| 2012/0109308 A1 | 5/2012 | Lechmann et al. |
| 2012/0130496 A1 | 5/2012 | Duffield et al. |
| 2012/0165945 A1 | 6/2012 | Hansell et al. |
| 2012/0185049 A1 | 7/2012 | Varela |
| 2012/0209386 A1 | 8/2012 | Triplett et al. |
| 2012/0215313 A1 | 8/2012 | Saidha et al. |
| 2012/0226357 A1 | 9/2012 | Varela |
| 2012/0265309 A1 | 10/2012 | Glerum et al. |
| 2012/0277861 A1 | 11/2012 | Steele et al. |
| 2012/0277870 A1 | 11/2012 | Wolters et al. |
| 2012/0323329 A1 | 12/2012 | Jimenez et al. |
| 2012/0330426 A1 | 12/2012 | Mclaughlin et al. |
| 2013/0023993 A1 | 1/2013 | Weiman |
| 2013/0023994 A1 | 1/2013 | Glerum |
| 2013/0158663 A1 | 6/2013 | Miller et al. |
| 2013/0158669 A1 | 6/2013 | Sungarian et al. |
| 2013/0197647 A1 | 8/2013 | Wolters et al. |
| 2013/0211526 A1 | 8/2013 | Alheidt et al. |
| 2013/0274883 A1 | 10/2013 | McLuen et al. |
| 2014/0067071 A1 | 3/2014 | Weiman et al. |
| 2014/0088714 A1 | 3/2014 | Miller et al. |
| 2014/0163683 A1 | 6/2014 | Seifert et al. |
| 2015/0066145 A1 | 3/2015 | Rogers et al. |
| 2015/0088258 A1 | 3/2015 | Jimenez et al. |
| 2015/0134064 A1 | 5/2015 | Grotz et al. |
| 2015/0216676 A1 | 8/2015 | Shulock et al. |
| 2015/0289988 A1 | 10/2015 | Ashley et al. |
| 2015/0374508 A1 | 12/2015 | Sandul |
| 2016/0166396 A1 | 6/2016 | McClintock |
| 2016/0324654 A1 | 11/2016 | Loebl et al. |
| 2017/0100258 A1 | 4/2017 | Jimenez et al. |
| 2017/0119543 A1 | 5/2017 | Dietzel et al. |
| 2019/0269521 A1 | 9/2019 | Shoshtaev |
| 2020/0093609 A1* | 3/2020 | Shoshtaev ............ A61F 2/4425 |
| 2022/0008212 A1 | 1/2022 | Weiman et al. |

FOREIGN PATENT DOCUMENTS

| | | |
|---|---|---|
| DE | 4327054 C1 | 4/1995 |
| EP | 0576379 B1 | 6/1993 |
| EP | 0610837 B1 | 7/1994 |
| EP | 3111896 A1 | 1/2017 |
| EP | 3818964 A1 | 5/2022 |
| EP | 4292570 A1 | 12/2023 |
| FR | 2794968 A1 | 12/2000 |
| JP | 2000-513263 A | 10/2000 |
| JP | 2021514760 A | 6/2021 |
| JP | 202216391 A | 1/2022 |
| KR | 200290058 | 9/2002 |
| KR | 200290058 Y1 | 9/2002 |
| SU | 1424826 A1 | 9/1988 |
| WO | 9201428 A1 | 2/1992 |
| WO | 9525485 A1 | 9/1995 |
| WO | 1999042062 A1 | 8/1999 |
| WO | 1999066867 A1 | 12/1999 |
| WO | 2002045625 A1 | 6/2002 |
| WO | 2004019829 A1 | 3/2004 |
| WO | 2004069033 A2 | 8/2004 |
| WO | 2006045094 A2 | 4/2006 |
| WO | 2006047587 A2 | 5/2006 |
| WO | 2006113080 A2 | 10/2006 |
| WO | 2008044057 A1 | 4/2008 |
| WO | 2008134515 A1 | 11/2008 |
| WO | 2009114381 A1 | 9/2009 |
| WO | 2010103344 A1 | 9/2010 |
| WO | 2012031267 A1 | 3/2012 |
| WO | 2015009793 A1 | 1/2015 |
| WO | 2022192512 A1 | 9/2022 |

* cited by examiner

EXPANDABLE FOOTPRINT IMPLANT

This application is a continuation application of U.S. patent application Ser. No. 18/124,095 filed on Mar. 21, 2023, which is incorporated in its entirety herein.

FIELD OF THE INVENTION

The present disclosure generally relates to devices and methods for promoting an intervertebral fusion, and more particularly relates to expandable fusion devices capable of being inserted between adjacent vertebrae to facilitate the fusion process and related systems and methods.

BACKGROUND OF THE INVENTION

A common procedure for handling pain associated with intervertebral discs that have become degenerated due to various factors, such as trauma or aging, is the use of intervertebral fusion devices for fusing one or more adjacent vertebral bodies. Generally, to fuse the adjacent vertebral bodies, the intervertebral disc is first partially or fully removed. An intervertebral fusion device is then inserted between neighboring vertebrae to maintain normal disc spacing and restore spinal stability, thereby facilitating an intervertebral fusion.

There are a number of fusion devices and methodologies for accomplishing the intervertebral fusion. These may include solid bone implants, fusion devices which include a cage or other implant mechanism, which may be packed with bone and/or bone growth inducing substances, and expandable implants. For example, posterior implants may be implanted to provide disc height restoration. The implants may be installed between adjacent vertebral bodies in order to fuse the vertebral bodies together, thereby alleviating the associated pain.

There are drawbacks, however, with existing posterior implants including subsidence and sagittal balance issues. As such, there exists a need for fusion devices capable of being installed inside an intervertebral disc space at a minimum height and width with an expandable footprint to address the subsidence issue and an adjustable lordosis to address the sagittal balance issue.

SUMMARY OF THE INVENTION

To meet this and other needs, devices, systems, and methods for performing intervertebral fusion and spine stabilization are provided. In particular, expandable intervertebral implants, for example, for posterior spinal surgery may be used to treat a variety of patient indications. The expandable implants are configured to increase the overall footprint size after being inserted into the disc space while also adjusting the lordosis and overall height. The in-situ expandable footprint or surface area is configured to address the subsidence issue and in-situ adjustable lordosis is configured to address the sagittal balance issue. The intervertebral implant may be combined with a posterior stabilization system, for example, including pedicle screws and spinal rod(s) to further stabilize the spine.

According to one embodiment, an expandable intervertebral implant includes a central drive assembly and left and right side assemblies. The central drive assembly includes a central drive screw positioned through a front plate, the central drive screw threadedly engaged to a central actuator, the central actuator coupled to a threaded sleeve, and the threaded sleeve positioned through a rear plate and threadedly engaged with a drive nut. The left and right side assemblies each include upper and lower endplates, a side actuator, and a front ramp. The side actuator and front ramp are slidably engaged with the upper and lower endplates. Rotation of the drive nut expands the implant in width and rotation of the drive screw expands the implant in height.

The expandable intervertebral implant may include one or more of the following features. The drive nut may pull the threaded sleeve and central actuator toward the rear plate and push the left and right side portions outwards in width. The drive screw may pull the front ramp toward the central actuator which then expands the upper and lower endplates in height. The central actuator may include a tubular body with an inner bore and a pair of opposite wings configured to mate with the side actuators. The rear plate may include a pair of female horizontal ramps defined into top and bottom surfaces of the rear plate, and the side actuator may include a pair of horizontal male ramps configured to interface with the female horizontal ramps of the rear plate. The front plate may include a pair of female horizontal ramps defined into top and bottom surfaces of the front plate, and the front ramp may include a pair of male horizontal ramps configured to interface with the female horizontal ramps of the front plate.

According to one embodiment, an expandable intervertebral implant includes a front plate having a central through bore, a central drive screw having an enlarged head and a threaded shaft positioned through the bore in the front plate, a central actuator having a tubular body with a through bore and a pair of opposed wings, the threaded shaft of the central drive screw threadedly engaged within one end of the bore of the central actuator, a rear plate having a central through bore, a threaded sleeve positioned through the bore in the rear plate and threadedly engaged with an opposite end of the bore of the central actuator, a drive nut threadedly engaged with the threaded sleeve, and left and right side assemblies each including upper and lower endplates, a side actuator, and a front ramp. The side actuator and front ramp are slidably engaged with the upper and lower endplates, the side actuator is slidably engaged with the rear plate and central actuator, and the front ramp is slidably engaged with the front plate.

The expandable intervertebral implant may include one or more of the following features. The left and right side assemblies may have a laterally collapsed configuration having a first width and a laterally expanded configuration having a second width, and the left and right side assemblies may have a vertically collapsed configuration having a first height and a vertically expanded configuration having a second height. The pair of opposed wings may each define a female ramp configured to receive a corresponding male ramp from the side actuator. The pair of opposed wings may be angled distally toward the front plate. The rear plate may include a cylindrical ring projecting proximally. The cylindrical ring may define an outer threaded surface. The threaded sleeve may include a first proximal exterior threaded section configured to interface with inner threads in a bore of the drive nut, and a second distal exterior threaded section configured to interface with inner threads in the bore of central actuator. The central drive screw may be retained in the front plate with a retaining ring. The drive nut may be retained in the rear plate with a retaining sleeve.

According to another embodiment, an expandable intervertebral implant includes a central drive assembly and a side assembly. The central drive assembly includes a front plate, a central drive screw, a central actuator, a threaded sleeve, a rear plate, and a drive nut aligned along a central longitudinal axis. The central drive screw is retained in the front plate. The central actuator is threadedly engaged with the central drive screw and the threaded sleeve. The threaded sleeve is retained in the rear plate and threadedly engaged with the drive nut. The side assembly includes upper and lower endplates, a side actuator, and a front ramp. The side actuator and front ramp are slidably engaged with the upper and lower endplates. The side actuator is slidably engaged with the rear plate and central actuator, and the front ramp is slidably engaged with the front plate. When actuated, the drive nut controls width expansion of the implant and the drive screw controls height expansion of the implant.

The expandable intervertebral implant may include one or more of the following features. The central drive screw may extend from a proximal end to a distal end where the distal end includes an enlarged head portion and the proximal end defines an instrument recess. The drive nut may define a central through bore and a proximal face of the drive nut may define an instrument recess different from the instrument recess of the central drive screw. The central drive screw may be located at a distal end of the implant and the drive nut may be located at a proximal end of the implant. When actuated, the drive nut may pull the threaded sleeve and central actuator proximally, thereby causing an expansion in width. When actuated, the central drive screw may pull the front plate toward the central actuator and pull the front ramp toward the side actuator, thereby causing an expansion in height.

According to another embodiment, a method of assembling an expandable intervertebral implant may include one or more of the following steps in any suitable order: (1) placing two front ramps onto a front plate by aligning mating ramps or slides; (2) placing one side actuator onto a rear plate by aligning mating ramps or slides; (3) placing a central actuator onto the side actuator and placing a second side actuator onto the rear plate and the central actuator by aligning the ramps or slides; (4) assembling each of the left and right side assemblies by placing a lower endplate onto the side actuator and placing an upper endplate onto the side actuator; (5) placing the front ramp into both the lower and upper endplates; (6) inserting a threaded sleeve through the rear plate and into the central actuator; (7) placing a friction ring onto the drive nut; (8) threading the drive nut onto the threaded sleeve; (9) pressing a retaining sleeve into the rear plate to secure the drive nut; (10) placing a friction ring onto a central drive screw; (11) inserting the central drive screw through the front plate and threading into the central actuator; and (12) placing a retaining ring into the front plate to secure the central drive screw.

According to another embodiment, a spinal fixation system includes an expandable intervertebral implant, a bone fastener, and a spinal rod attachable to the bone fastener. The expandable intervertebral implant comprising a central drive assembly and left and right side assemblies, the central drive assembly including a front plate, a central drive screw, a central actuator, a threaded sleeve, a rear plate, and a drive nut, and the left and right side assemblies each including upper and lower endplates, a side actuator, and a front ramp, wherein rotation of the drive nut is configured to expand the implant in width and rotation of the drive screw is configured to expand the implant in height.

The spinal fixation system may include one or more of the following features. The expandable intervertebral implant may be configured to be installed through a transforaminal lumbar interbody fusion procedure. The bone fastener may include a threaded shaft and a tulip head. The bone fastener may be a polyaxial bone screw. The bone fastener may be a pedicle screw. The plurality of bone fasteners may be configured to be installed in vertebrae adjacent to the expandable intervertebral implant. The system may include a set of screws and rods configured to stabilize the spine.

According to another embodiment, a spinal fixation system includes an expandable intervertebral implant comprising a central drive assembly and left and right side assemblies, and a posterior stabilization system. The central drive assembly includes a front plate having a central through bore, a central drive screw having an enlarged head and a threaded shaft positioned through the bore in the front plate, a central actuator having a tubular body with a through bore and a pair of opposed wings, the threaded shaft of the central drive screw threadedly engaged within one end of the bore of the central actuator, a rear plate having a central through bore, a threaded sleeve positioned through the bore in the rear plate and threadedly engaged with an opposite end of the bore of the central actuator, and a drive nut threadedly engaged with the threaded sleeve. The left and right side assemblies each include upper and lower endplates, a side actuator, and a front ramp.

The spinal fixation system may include one or more of the following features. The posterior stabilization system may include a plurality of bone fasteners including a threaded shaft and a tulip head. The plurality of bone fasteners may be configured to be inserted into pedicles of adjacent vertebrae. The posterior stabilization system may include a spinal rod affixed to the tulip heads of the bone fasteners to stabilize a portion of the spine. Actuation of the drive nut may be configured to expand the intervertebral implant in width. Actuation of the central drive screw may be configured to expand the intervertebral implant in height in-situ.

According to yet another embodiment, a method of spinal fixation may include one or more of the following steps in any suitable order: (1) inserting an expandable intervertebral implant into a disc space between adjacent vertebrae, the expandable implant comprising a central drive assembly and left and right side assemblies, the central drive assembly includes a front plate, a central drive screw, a central actuator, a threaded sleeve, a rear plate, and a drive nut, and the left and right side assemblies each include upper and lower endplates, a side actuator, and a front ramp; (2) expanding the implant in width and/or height; (3) affixing bone screws to pedicles of adjacent vertebrae; and (4) connecting a spinal rod between the bone screws. The method may further include expanding the implant in width by rotating the drive nut and expanding the implant in height by rotating the central drive screw. The implant may be expanded in width to increase an overall footprint size, thereby minimizing a potential for implant subsidence. The implant may be expanded in height in-situ to adjust lordosis. Before inserting the expandable intervertebral implant into the disc space, accessing a posterior aspect of a spine, and performing a facetectomy. A unilateral facetectomy may be performed to allow for visualization and removal of a disc. A first set of bone screws may be affixed to pedicles of the vertebrae, and a first spinal rod is connected therebetween, a second set of bone screw may be affixed to opposite pedicle of the vertebrae, and a second spinal rod is connected therebetween.

According to yet another embodiment, a kit may include a plurality of implants of different sizes and configurations. The kit may further include one or more devices suitable for installing and/or removing the implants and systems described herein, such as insertion devices or drivers; one or more removal devices; and other tools and devices, which may be suitable for surgery.

BRIEF DESCRIPTION OF THE DRAWINGS

The present embodiments will become more fully understood from the detailed description and the accompanying drawings, wherein.

DETAILED DESCRIPTION

Embodiments of the disclosure are generally directed to devices, systems, and methods for intervertebral fusion and spine stabilization. Specifically, expandable implants are configured to increase the overall footprint size after being inserted into the disc space while also adjusting the lordosis and overall height. The expandable implants may include one or more side assemblies configured to expand in width and in height. In doing so, the expansion addresses sagittal balance correction and subsidence issues. The intervertebral implant may be combined with a posterior stabilization system, for example, including pedicle screws and spinal rod(s) to further stabilize the spine.

A spinal fusion is typically employed to eliminate pain caused by motion of degenerated disc material. Upon successful fusion, a fusion device becomes permanently fixed within the intervertebral disc space. The expandable fusion device may be positioned between adjacent vertebral bodies in a collapsed position. The expandable fusion device is configured to expand in width and subsequently in height. The fusion device engages the endplates of the adjacent vertebral bodies and, in the installed position, maintains desired intervertebral disc spacing and restores spinal stability, thereby facilitating the intervertebral fusion.

Minimally invasive surgery (MIS) may be used to preserve muscular anatomy by only causing disruption where necessary. The benefit of the MIS surgical approach is that it can reduce post-operative pain and improve recovery time for patients. In one embodiment, the expandable fusion device can be configured to be placed down an endoscopic tube and into the surgical target site. By way of example, the surgical site may be an intervertebral disc space situated between two adjacent vertebrae. Although particularly suited for use in a transforaminal lumbar interbody fusion (TLIF), it will be readily appreciated by those skilled in the art that the implant may be employed in any number of suitable orthopedic approaches and procedures, including but not limited to, anterior, posterior, lateral, anterolateral, or posterolateral approaches to the lumbar spine, cervical spine, or thoracic spine, as well as any non-spine application, such as treatment of bone fractures and the like.

Components of all of the devices disclosed herein may be manufactured of any suitable materials including metals (e.g., titanium), metal alloys (e.g., stainless steel, cobalt-chromium, and titanium alloys), ceramics, plastics, plastic composites, or polymeric materials (e.g., polyether ether ketone (PEEK), polyphenylene sulfone (PPSU), polysulfone (PSU), polycarbonate (PC), polyetherimide (PEI), polypropylene (PP), polyacetals, or mixtures or co-polymers thereof), and/or combinations thereof. In some embodiments, the devices may include radiolucent and/or radiopaque materials. The components can also be machined and/or manufactured using any suitable techniques (e.g., 3D printing).

Figure 1A:
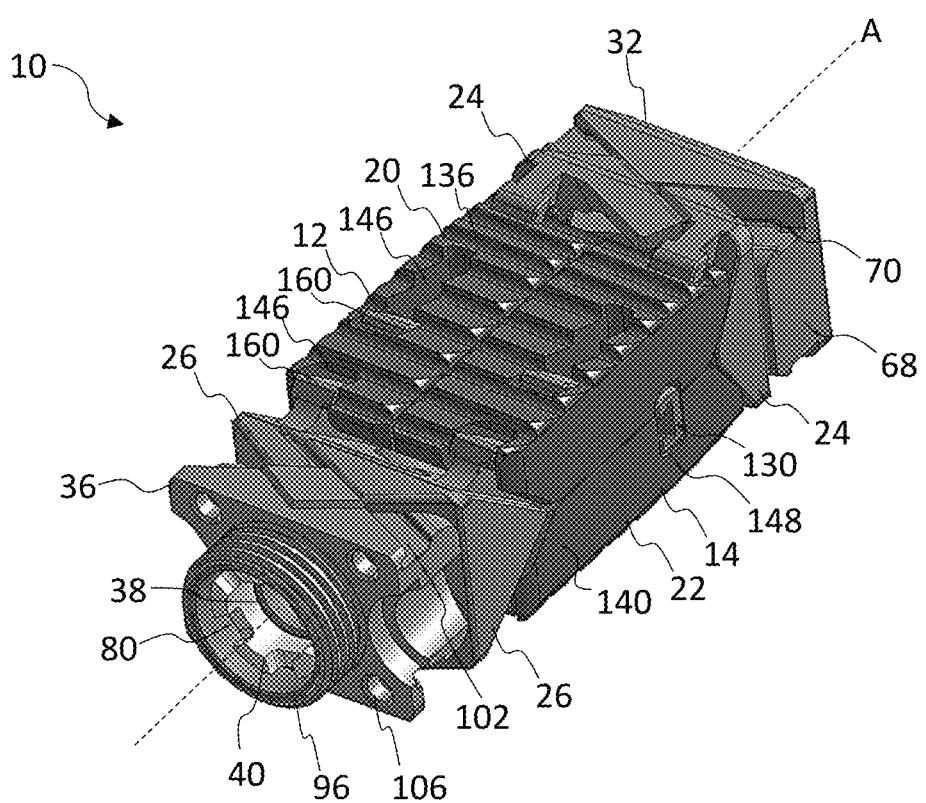
FIGS. 1A-1C illustrate perspective views of an expandable implant in a collapsed position, expanded in width, and expanded in width and height, respectively, according to one embodiment.
Figure 1B:
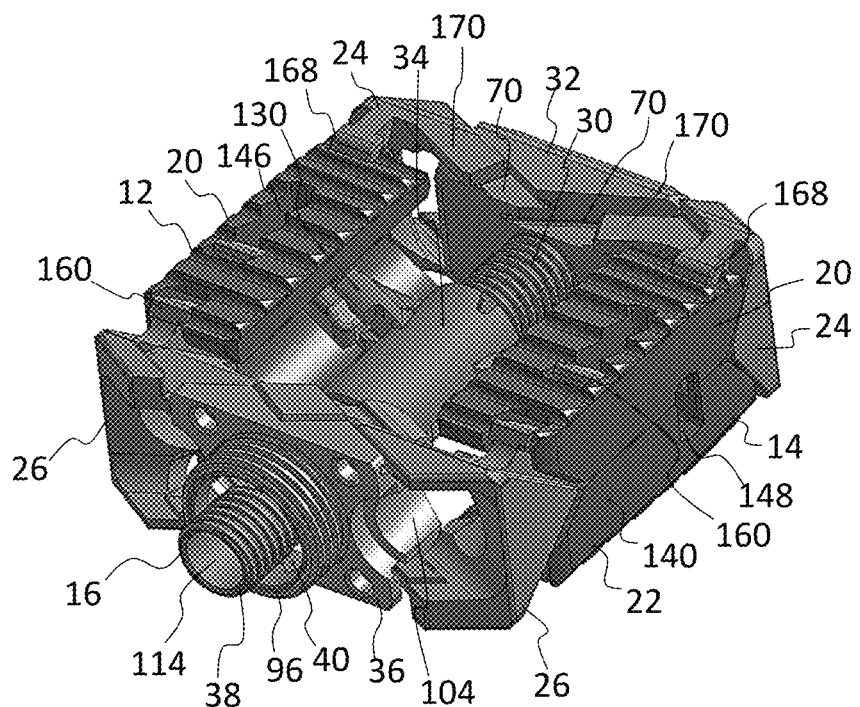
Figure 1C:
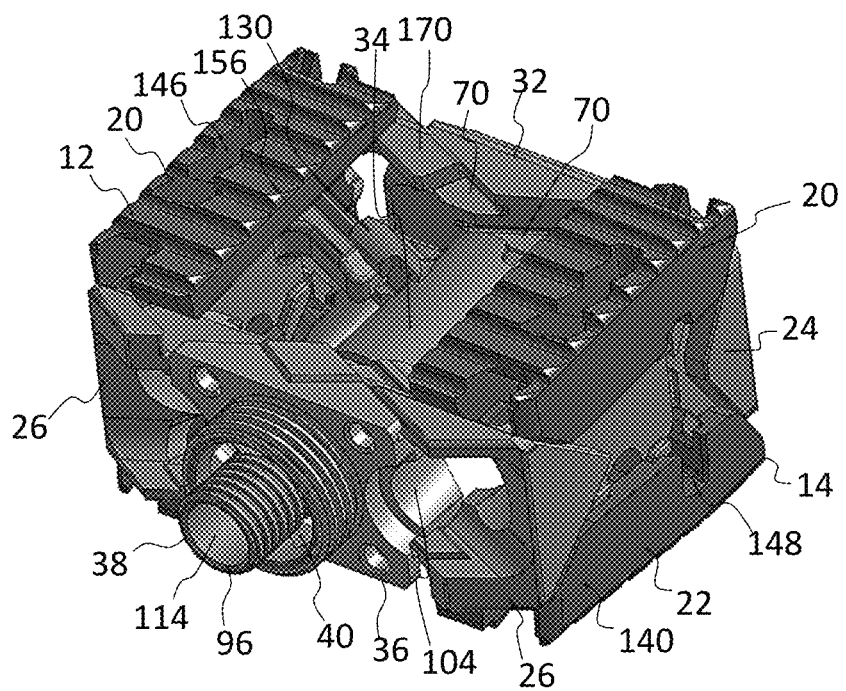

Turning now to the drawing, where like reference numerals refer to like elements, FIGS. 1A-1C illustrate an expandable fusion device or implant 10 according to one embodiment. The expandable fusion device 10 may include left and right side portion assemblies 12, 14 configured to expand in width to increase the overall footprint of the device 10 and expand in height to correct disc height restoration, lordosis, and/or sagittal balance. The implant 10 may be suitable for a transforaminal lumbar interbody fusion (TLIF) through a posterior approach or other suitable surgical procedure.

The expandable fusion device 10 extends along a central longitudinal axis A between front and rear ends of the device 10. FIG. 1A shows the expandable fusion device 10 in a fully collapsed configuration with the left and right side portions 12, 14 collapsed in both width and height. FIG. 1B shows the expandable fusion device 10 in an expanded configuration with the left and right side portions 12, 14 expanded in width. FIG. 1C shows the expandable fusion device in a fully expanded configuration with the left and right side portions 12, 14 expanded in width and in height. It should be understood that references to the front and rear ends and left and right side portions 12, 14 are described with respect to the direction of placement into an intervertebral disc space with the front of the expandable fusion device 10 placed into the disc space first, followed by the rear of the expandable fusion device 10. These and other directional terms may be used herein for descriptive purposes and do not limit the orientation(s) in which the devices may be used.

Figure 2:
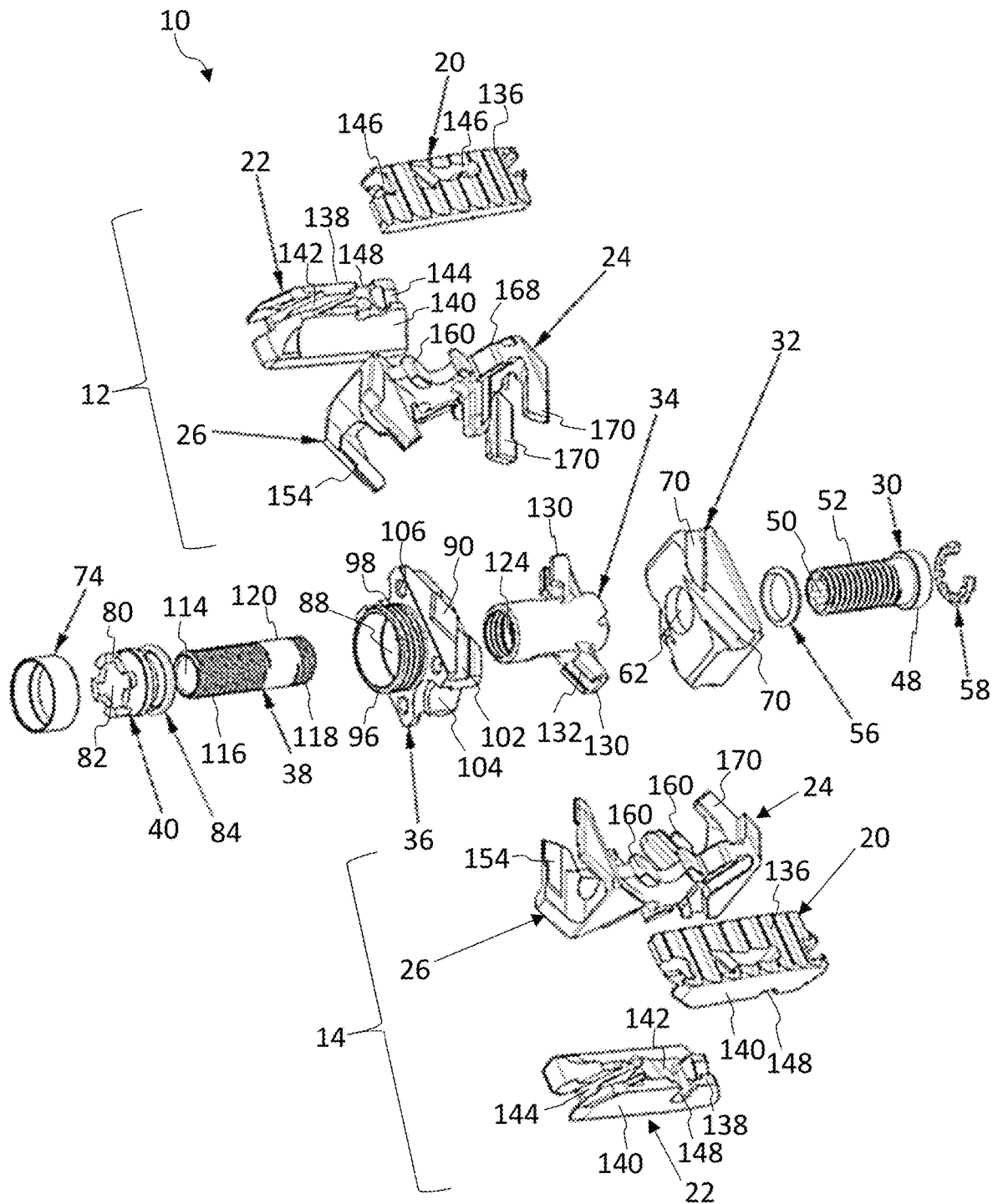
FIG. 2 shows an exploded view of the expandable implant of FIGS. 1A-1C.

With emphasis on the exploded view in FIG. 2, the implant 10 includes a first half or left side portion 12, a second half or right side portion 14, and a central drive assembly 16. The left and right side portion assemblies 12, 14 may each include upper and lower endplates 20, 22, a front ramp 24, and a side actuator 26. The central drive assembly 16 includes a central drive screw 30, a front plate 32, a central actuator 34, a rear plate 36, a central threaded sleeve 38, and a central drive nut 40 aligned along the central longitudinal axis A. The left and right side portions 12, 14 are expanded in width by the central drive nut 40. The upper and lower endplates 20, 22 are expanded in height by the central drive screw 30.

In particular, the left and right side portions 12, 14 are controllable by the central drive nut 40 which is attached to the central threaded sleeve 38 and central actuator 34. The drive nut 40 pulls the threaded sleeve 38 and central actuator 34 toward the rear plate 36 and pushes the left and right side portions 12, 14 outwards with the uses of ramps or slides 70, 102, 132, 154, 156, 170. Once the left and right side portions 12, 14 are fully expanded in width, the front plate 32 is controllable by the central drive screw 30. The central drive screw 30 pulls the front plate 20 toward the central actuator 34 while also pulling the front ramps 24 toward the side actuators 26. Each side assembly 12, 14 has upper and lower endplates 20, 22, front ramp 24, and side actuator 26. The front ramp 24 is actuated while the drive screw 30 is turned. This pulls the front ramp 24 toward the side actuator 26 which then expands the top and bottom endplates 20, 22 up and down with mating ramps 142, 160, 168 on the front ramps 24 and side actuators 26.

Figure 3:
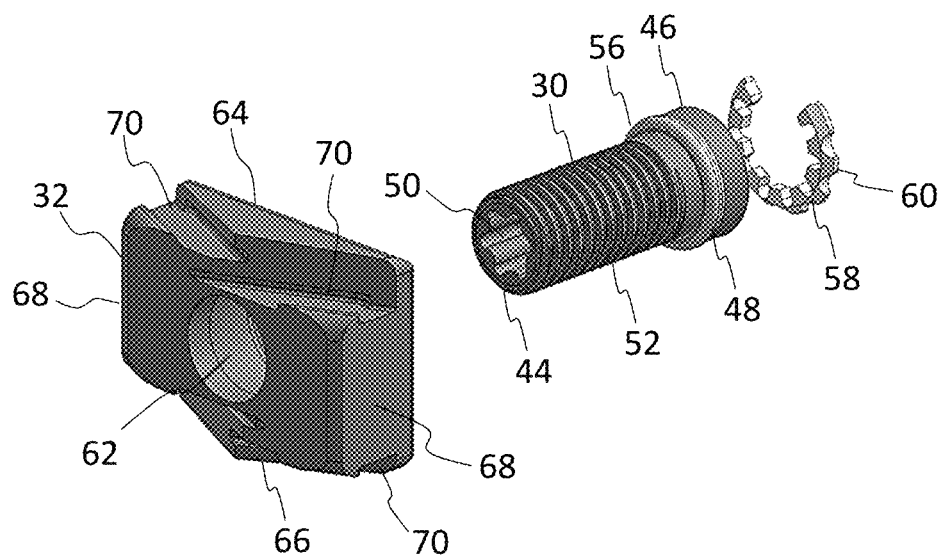
FIG. 3 shows an exploded view of a portion of the central drive assembly including a central drive screw insertable into a front plate and configured to be retained by a retaining ring according to one embodiment.

As best seen in FIG. 3, the central drive screw 30 extends from a proximal end 44 to a distal end 46. The distal end 46 may include an enlarged head portion 48 configured to be received in a bore 62 defined through the front plate 32. The enlarged head 48 may include a wide cylindrical head with a smooth outer surface at the distal end of the central drive screw 30. The proximal end 44 of the drive screw 30 may define an instrument recess 50 configured to receive an instrument, such as a driver, to rotate or actuate the drive screw 30. The instrument recess 50 may include a tri-lobe, hex, star, or other suitable recess configured to engage with a driver instrument to apply torque to the drive screw 30. The drive screw 30 may include a shaft with an exterior threaded portion 52 extending along its length. The exterior threads 52 may extend from the proximal end 44 to a location near the bottom of the enlarged head 48. The drive screw 30 is receivable through the bore 62 in the front plate 32 such that the enlarged head portion 48 of the drive screw 30 is receivable in the front plate 32. An optional friction ring 56, such as a polyether ether ketone (PEEK) ring, may be assembled onto the drive screw 30, for example, below the enlarged head 48, to increase friction or drag on the drive screw 30 during rotation.

The central drive screw 30 is inserted into the front plate 32 and may be retained within the front plate 32 using a retaining ring 58. The drive screw 30 controls height expansion of the implant 10 when actuated. The retaining ring 58 may include a split ring with a plurality of inner and/or outer teeth 60 or various reliefs to allow the retaining ring 58 to compress and enter the bore 62 of the front plate 32 and engage an internal groove. The retaining ring 60 may include two slots, for example, to be engaged with an instrument to aid insertion and removal of the retaining ring 58. When the retaining ring 58 is positioned around the drive screw 30 and within the bore 62 in the front plate 32, the teeth 58 are configured to engage with the central drive screw 30, thereby locking the screw 30 in position in the plate 32.

The front plate 32 defines a central bore 62 therethrough configured to receive drive screw 30. The axis of bore 62 is aligned along central longitudinal axis A. The front plate 32 includes an upper face or top surface 64 and an opposite lower face or bottom surface 66 connected by side surfaces 68. The top and bottom surfaces 64, 66 may include one or more slides or ramps 70 configured to interface with corresponding ramps 170 on the front ramps 24 of the left and right side portions 12, 14. Slides or ramps 70 may include horizontal ramps defining female channels or grooves configured to receive the mating male counterparts 170 of the front ramps 24. It will be appreciated, however, that the female/male configurations may be reversed or may include other suitable ramp interactions, sliding features, or mating components to provide lateral expansion of the left and ride side portions 12, 14.

In one embodiment, the front plate 32 may include a first pair of horizontal ramps 70 defined into the top 64 of the front plate 32 and a second pair of horizontal ramps 70 defined into the bottom 66 of the front plate 32. Each of the ramps 70 may be aligned along distinct horizontal planes. In this manner, each ramp 70 has a constant depth along its length such that one of the female horizontal ramps has a depth greater than the other female horizontal ramp. For example, a first ramp 70 defined along the top 64 of the front plate 32 may be positioned along one given horizontal plane lower or higher relative to the other ramp 70 defined along the top 64 of the front plate 32. The horizontal ramps 70 may be angled, diagonal, or slanted such that one end of each ramp 70 begins at a side 68 of the front plate 32 and extend centrally in a direction toward the central actuator 34 with the ramps 70 leading toward one another. Although described as horizontal ramps to provide for horizontal or lateral expansion of the left and right side assemblies 12, 14, it will be appreciated that the horizontal ramps 70 may be sloped, slanted, or otherwise configured off axis to provide for a different trajectory or type of expansion.

Figure 4:
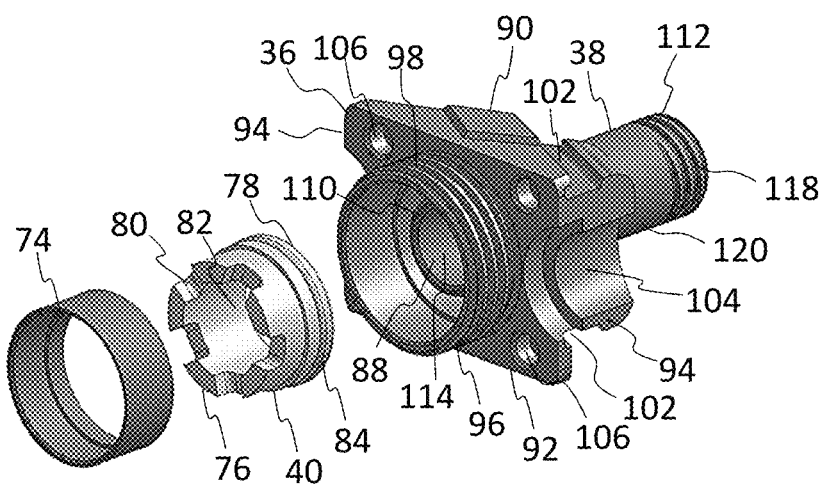
FIG. 4 shows an exploded view of another portion of the central drive assembly including a central drive nut, rear plate, threaded sleeve, and retaining sleeve for securing the drive nut in the rear plate according to one embodiment.

As best seen in FIG. 4, drive nut 40 is inserted into the rear plate 36 and may be retained using retaining sleeve 74. The drive nut 40 controls width expansion of the implant 10 when actuated. The drive nut 40 may have a generally cylindrical body that extends from a proximal end 76 to a distal end 78. The proximal face 76 may define one or more indentions or notches to form an instrument recess 80 configured to interface with an instrument, such as a driver, to rotate or actuate the drive nut 40. The instrument recess 80 may define a slotted, splined, tri-lobe, hex, star, other suitable recess, or a portion thereof configured to engage with a driver instrument to apply torque to the drive nut 40. The instrument recess 80 of the drive nut 40 may be of a different type than the instrument recess 50 of the drive screw 30 so the user can easily discern which component is intended to be actuated. In this manner, the instrument recess 80 is configured to engage with a driver instrument to apply torque to the drive nut 40, thereby driving width expansion of the left and right side assemblies 12, 14.

The drive nut 40 defines a central bore 82 such that another instrument is able to access the distal drive screw 30. The axis of through bore 82 may aligned along central longitudinal axis A. The drive nut 40 is receivable within the bore 88 in the rear plate 36 such that the body of the drive nut 40 is receivable in the rear plate 36. An optional friction ring 84, such as a polyether ether ketone (PEEK) ring, may be assembled onto the drive nut 40, for example, near distal end 78, to increase friction or drag on the drive nut 40 during rotation. The retaining sleeve 74 is pressed into the rear plate 36, thereby securing the drive nut 40 in the rear plate 36. The retaining sleeve 74 may include a ring or band sized and dimensioned to fit around the drive nut 40 and within the projection 96 of the rear plate 36.

The rear plate 36 defines a central bore 88 therethrough configured to receive drive nut 40 and threaded sleeve 38. The axis of bore 88 is aligned along central longitudinal axis A. The rear plate 36 includes an upper face or top surface 90 and an opposite lower face or bottom surface 92 connected by side surfaces 94. A projection 96 may extend proximally defining a substantially cylindrical ring with an outer threaded portion 98, for example, configured to threadedly engage with an implant insertion instrument. A threaded connection to the rear plate 36 provides for a rigid connection to the insertion instrument. The top and bottom surfaces 90, 92 may include one or more slides or ramps 102 configured to interface with corresponding ramps 154 on the side actuators 26 of the left and right side portions 12, 14.

The rear plate 36 includes one or more slides or ramps 102 configured to interface with corresponding ramps 154 on the actuators 26 of the left and right side portions 12, 14. For example, near the distal end of the rear plate 36, the rear plate 36 may include a pair of ramps 102 defined into each of the top and bottom surfaces 90, 92 of the rear plate 36. Similar to ramps 70, ramps 102 may be horizontal ramps aligned along one or more horizontal planes. For example, one of the pair of ramps 102 may be positioned along one given horizontal plane lower or higher relative to the other ramp 102 along another given horizontal plane. In other words, each ramp 102 has a constant depth along its length such that one ramp 102 has a depth greater than the other ramp 102. The horizontal ramps 102 may be angled, diagonal, or slanted such that one end of the ramp 102 starts at a side 94 of the rear plate 36 and extends toward the center of the rear plate 36 with the ramps 102 leading toward one another. The horizontal ramps 102 may define female channels or grooves configured to receive the mating male counterparts 154 of the actuators 26. It will be appreciated, however, that the female/male configurations may be reversed or may include other suitable ramp interactions, sliding features, or mating components to provide lateral expansion of the left and right side portions 12, 14.

The rear plate 36 may include one or more instrument recesses or slots 104, 106 configured to be engaged by an instrument, such as an insertion instrument, or allow for access to the implant 10. For example, the side faces 94 of the rear plate 36 may each include side recesses or instrument slots 104 configured to receive a graft delivery device. For example, opposite sides 94 of the rear plate 36 may include two opposed semi-circular recesses 104 configured to allow the graft delivery device to enter the central portion of the implant 10 once fully expanded in width and/or height. Bone graft or similar bone growth inducing material can be introduced within and/or around the fusion device 10 to further promote and facilitate the intervertebral fusion. In addition, one or more recesses 106 may be positioned about the proximal face of the rear plate 36. These circular recesses 106 may be aligned at the four corners of the plate 36. The quadruple recesses 106 may help to align an instrument, such as insertion instrument.

The drive nut 40 is threaded onto threaded sleeve 38. The threaded sleeve 38 is positioned through bore 88 of rear plate 36 and threadedly engaged to drive nut 40. The threaded sleeve 38 is a cylindrical sleeve or shaft sleeve defining a central through bore 114 between proximal end 110 and distal end 112 of the sleeve 38. The axis of the central bore 114 aligns with the central longitudinal axis A. An outer surface of the sleeve 38 includes exterior threaded sections 116, 118. A first proximal exterior threaded section 116 is configured to interface with inner threads in bore 82 of drive nut 40. A second distal exterior threaded section 118 is configured to interface with inner threads in bore 124 of central actuator 34. The threaded sections 116 may include helically wound thread forms having any suitable lead, pitch, handedness, angle, diameters, etc. The separate thread sections 116, 118 may have the same or different thread types. The thread sections 116, 118 may be separated by a non-threaded or smooth section 120. The proximal threaded section 116 may be longer than the distal threaded section 118 such that the non-threaded section 120 is located closer to the distal end 112 of the sleeve 38. For example, the length of the proximal threaded section 116 may be double, triple, quadruple, or greater than the length of the distal threaded section 118.

Figure 5:
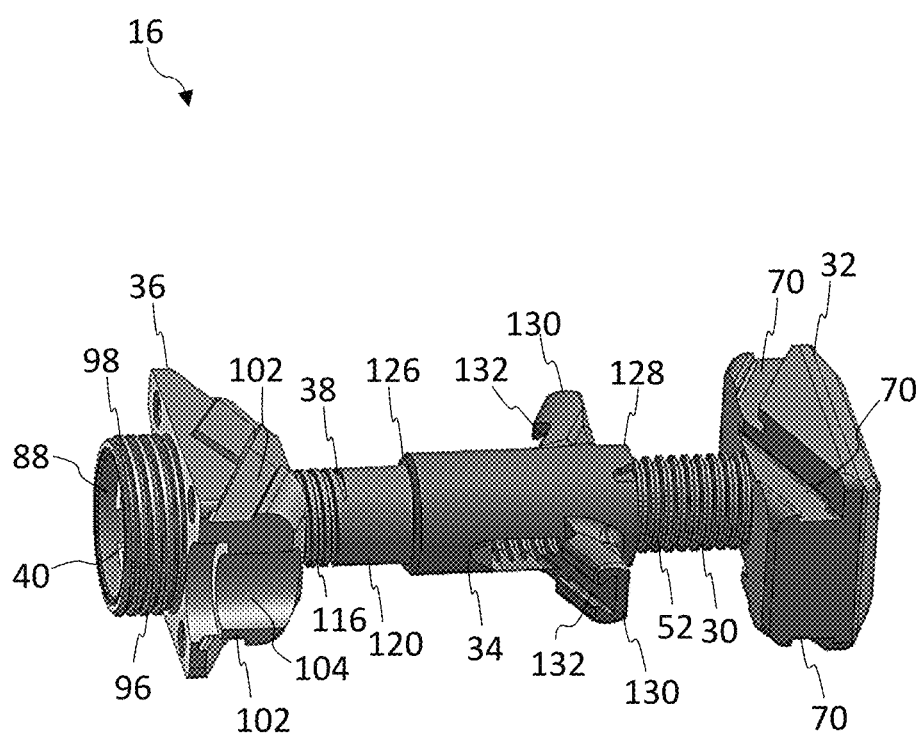
FIG. 5 shows the central drive assembly including the rear plate attached to the drive sleeve, the drive sleeve attached to the central actuator, the central actuator attached to the central drive screw, and the central drive screw attached to the front plate according to one embodiment.

Turning now to FIG. 5, the fully assembled central drive assembly 16 is shown. The threaded sleeve 38 is attached to central actuator 34. The central actuator 34 includes a tubular body with an inner bore 124 extending from a proximal end 126 to a distal end 128. The inner bore 124 of the central actuator 34 is internally threaded to allow for threaded engagement with the distal threaded section 118 of the threaded sleeve 38 and the threaded shaft 52 of the drive screw 30. The central actuator 34 includes a pair of opposite wings 130 extending from an outer surface of the tubular body. Each wing 130 may terminate at a distal free end. The wings 130 may be angled such that the distal free ends of the wings 130 point toward the front plate 32. Each wing 130 may define one or more slides or ramps 132 configured to mate with corresponding surfaces on the side actuators 26. The ramps 132 may be angled, diagonal, chamfered, or slanted such that one end of the ramp 132 starts at the body of the central actuator 34 and extends to the free end of the respective wing 130. The ramps 132 may define female channels or grooves configured to receive the mating male counterparts 156 of the side actuators 26. The female ramps 132 may extend openly along a proximal face of each wing 130. It will be appreciated that the female/male configurations and locations may be reversed or changed to include other suitable ramp interactions, sliding features, or mating components to help provide lateral expansion of the left and right side portions 12, 14.

When the central drive assembly 16 is assembled, the proximal end 110 of the threaded sleeve 38 is positioned through the bore 88 in the rear plate 36. The drive nut 40 is threaded onto the proximal threaded section 116 of the threaded sleeve 38. The distal threaded section 118 of the threaded sleeve 38 is threaded into the central actuator 34. The actuation of the drive nut 40 is configured to push and pull the threaded sleeve 38 and central actuator 34 relative to the rear plate 36 and expand the implant 10 in width once fully assembled. The drive screw 30 is positioned through the bore 62 in the front plate 32. The threaded shaft 52 of the drive screw 30 is threaded into the distal end 128 of the central actuator 34, which is attached to the threaded sleeve 38. The actuation of the drive screw 30 is configured to push and pull the front plate 32 and front ramps 24 relative to the central actuator 34 and side actuators 26 and expand the implant 10 in height once fully assembled.

Figure 6:
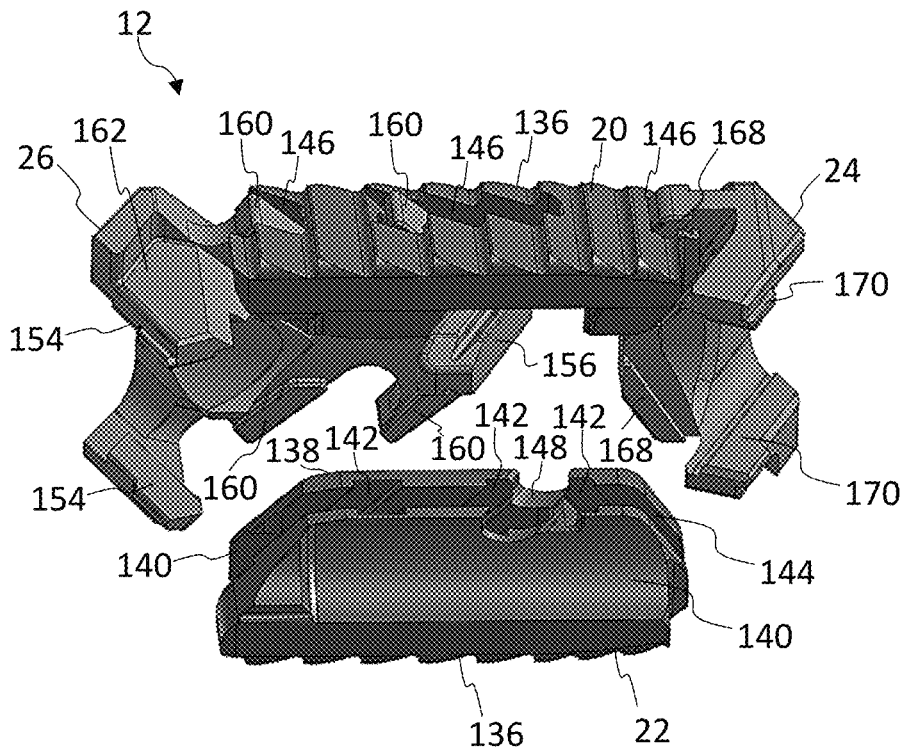
FIG. 6 shows a side assembly including the top endplate assembled onto the side actuator and the front ramp and a lower endplate configured to be placed onto the side actuator and front ramp during assembly.
Figure 7:
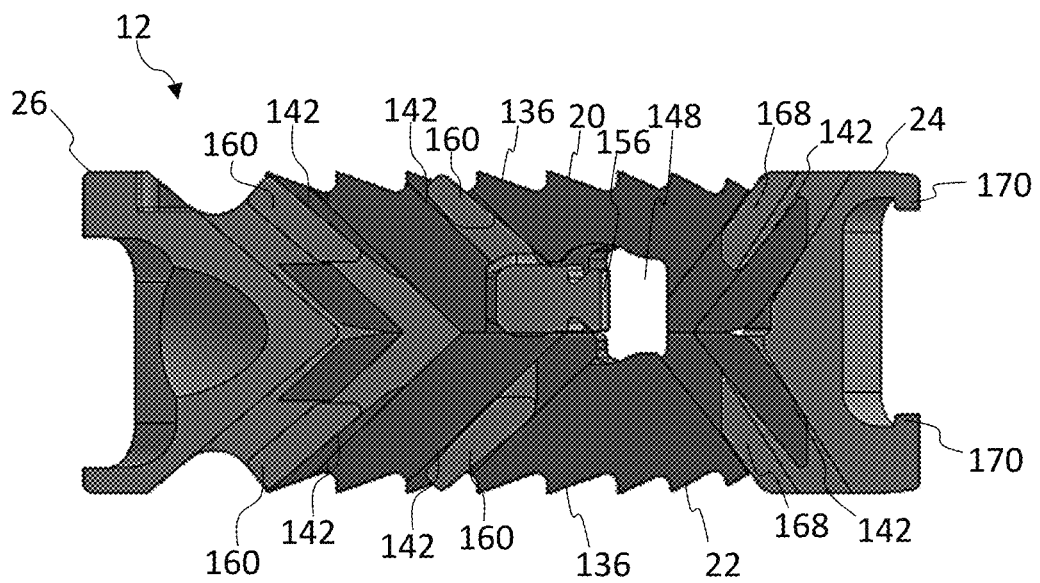
FIG. 7 shows a cross-sectional view of the ramps of the upper and lower endplates engaged with the side actuator and front ramp according to one embodiment.

Turning now to FIGS. 6 and 7, the left and right side assemblies 12, 14 are each assembled by placing the upper and lower endplates 20, 22 onto side actuator 26 and front ramp 24. The left and right side portion assemblies 12, 14 may each include upper and lower endplates 20, 22 configured to expand away from one another to increase the vertical height of the expandable fusion device 10. The upper and lower endplates 20, 22 may be the same or mirror images of one another. Although described with reference to assembly 12 and upper endplate 20, the discussion herein applies equally to assembly 14 and lower endplate 22. The upper endplate 20 includes an upper or outer facing surface 136 configured to interface with the vertebral endplate(s) of the adjacent vertebral bodies when implanted in the disc space. The outer surface 136 may include a plurality of teeth, ridges, roughened surfaces, keels, gripping or purchasing projections, or other friction increasing elements configured to retain the device 10 in the disc space. For example, the endplates 20, 22 may be 3D printed using additive manufacturing to provide a natural roughened surface to promote boney on growth or may be machined and blasted to achieve a roughened surface.

The upper endplate 20 includes a lower or inner facing surface 138 and one or more side walls 140 defining one or more slides or ramps 142 configured to interface with corresponding ramps 160, 168 on the actuator 26 and front ramp 24, respectively. For example, the upper endplate 20 may define a pair of sidewalls 140 forming a gap or channel 144 therebetween. The channel 144 may be generally U-shaped, J-shaped, C-shaped, or another suitable configuration. At least three pairs of ramps 142 may be defined within the channel 144 of the endplate 20. The ramps 142 may be vertical ramps aligned along one or more vertical planes. In one embodiment, all three pairs of vertical ramps 142 may be aligned along the same plane. Although vertically-oriented, the vertical ramps 142 may be angled, diagonal, or sloped to increase the vertical height of the endplates 20, 22.

In one embodiment, two pairs of vertical ramps 142 interfaced with the side actuator 26 may be angled in one direction and a third pair of vertical ramps 142 interfaced with the front ramp 24 may be angled in an opposite direction. For example, the distal-most vertical ramps 142, near front ramp 24, may be sloped such that they points toward the front ramp 24 as they extend along the side walls 140 from the inner surface 138 toward the outer surface 136. Similarly, the proximal-most vertical ramps 142, near the side actuator 26, and centrally located vertical ramps 142, may be sloped such that they point toward the side actuator 26 as they extend along the side walls 140 from the inner surface 138 toward the outer surface 136. The proximal-most vertical ramps 142 and central vertical ramps 142 may be aligned in parallel with the same degree of slope or may have different degrees of slope.

The vertical ramps 142 may define female channels or grooves configured to receive the mating male counterparts 160, 168 of the side actuator 26 and front ramp 24, respectively. It will be appreciated that the female/male configurations may be reversed or may include other suitable ramp interactions, sliding features, or mating components to provide vertical expansion of the left and ride side portions 12, 14. Although described as vertical ramps to provide for vertical expansion of the left and right side assemblies 12, 14, it will be appreciated that the vertical ramps 142 may be sloped, slanted, or otherwise configured off axis to provide for a different trajectory or type of expansion.

One or more openings 146 may extend vertically through the body of the endplate 20, 22. In the collapsed position, as shown in FIG. 1A, ramp portions 160 of the side actuators 26 may be received through the openings 146. Similarly, when expanded in width, as shown in FIG. 1B, the ramps 160 of the side actuators 26 are receivable through the openings 146 in the endplates 20, 22. In the vertically expanded position, as shown in FIG. 1C, the openings 146 may be open and free to receive bone-graft or other suitable bone forming material. One or more openings or slots 148 may extend horizontally through the sidewalls 140 of the endplate 20, 22. The slots 148 may be provided between the distal-most and central vertical ramps 142 and near the inner surface 138 of the endplate 20, 22. In the collapsed position, as shown in FIG. 1A, slots 148 from the upper and lower endplates 20, 22 may align such that the wings 130 of the central actuator 34 is positionable through the openings 148. When expanded in width, as shown in FIG. 1B, the side assemblies 12, 14 expand outward and away from one another and the openings 148 or a portion thereof are vacant.

Figure 8:
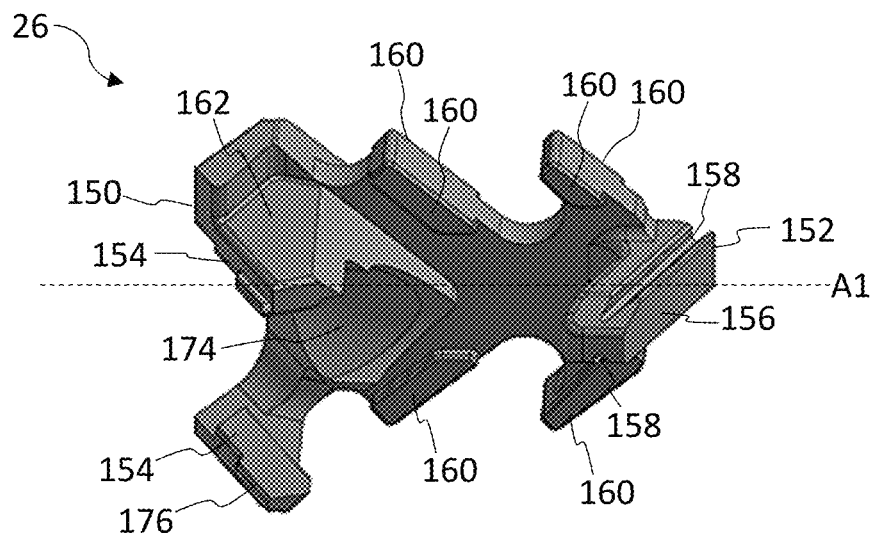
FIG. 8 shows the side actuator of the side assemblies according to one embodiment.

Turning now to FIG. 8, the left and right side portion assemblies 12, 14 may include first and second side actuators 26 positioned between the upper and lower endplates 20, 22 of the left and right side portions 12, 14, respectively. The actuator 26 may include a body extending along a central axis A1 from a proximal end 150 to a distal end 152. Central axis A1 may be generally parallel with central longitudinal axis A. The proximal end 150 may define one or more horizontal slides or ramps 154 configured to engage with the horizontal ramps 102 of the rear plate 36. The side actuator 26 may define a pair of top and bottom horizontal ramps 154 pointing inwardly toward one another. The horizontal ramps 154 may have an angled, diagonal, or slanted surface in a manner complimentary to the ramps 102 of the rear plate 36. In particular, the horizontal ramps 154 may define male projections configured to enter the female counterparts 102 of the rear plate 36. The ramp 154 may define a limiter 176 to end movement of the mating slides or ramps 102, 154. For example, the limiter 176 may include a widened ramp surface, a projection or protrusion, a bevel or dovetail, etc. configured to reduce or limit the relative movement between the ramps 102, 154.

The distal end 152 of the side actuator 26 may include ramp 156 configured to engage with the corresponding ramp 132 on the wing 130 of the central actuator 34. The side actuator 26 may define upper and lower grooves 158 to form a single male ramp 156 pointing distally. The male ramp 156 may have an angled, diagonal, or slanted surface in a manner complimentary to the female ramp 132 on wing 130 of the central actuator 34. This slidable interface 132, 156 may be configured to help guide the outward expansion in width of the first and second side assemblies 12, 14.

The actuator 26 includes a plurality of ramps 160 configured to engage with the endplates 20, 22. The actuator 26 may define a plurality of vertical ramps 160 configured to engage with the vertical ramps 142 of the endplates 20, 22. The actuator 26 may define a first set of vertical ramps 160 slanted upwardly toward the proximal end 150 or downwardly toward the distal end 152 and a second set of vertical ramps 160 slanted upwardly toward the distal end 152 or downwardly toward the proximal end 150 of the actuator 26. Each set of ramps 160 may define a pair of male projections configured to enter the female counterparts 142 of the endplates 20, 22. The vertical ramps 160 may have an angled, diagonal, or sloped surface in a manner complimentary to the corresponding ramps 142 of the endplates 20, 22.

Figure 9:
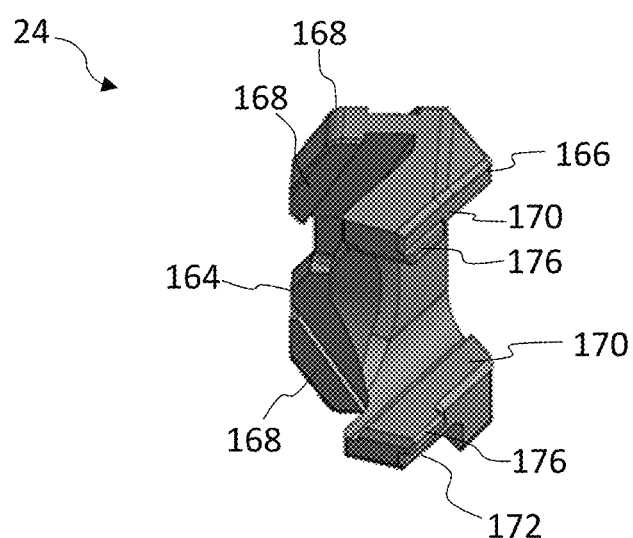
FIG. 9 shows the front ramp of the side assemblies according to one embodiment.

As shown in FIG. 9, the left and right side portions 12, 14 may each include front ramp 24 configured to expand the distal or front ends of the upper and lower endplates 20, 22. The front ramp 24 may include a body extending from a proximal end 164 to a distal end 166. The proximal end 164 may define one or more vertical ramps 168 configured to engage with the vertical ramps 142 of the endplates 20, 22. The front ramp 24 may define first vertical ramps 168 sloped downwardly toward the proximal end 164 and a second vertical ramp 168 sloped upwardly toward the proximal end 164 of the front ramp 24. Each of ramps 168 may define a pair of opposed male projections configured to enter the female counterparts 142 in the channel 144 of the endplates 20, 22. The vertical male ramps 168 may have an angled, diagonal, or sloped surface in a manner complimentary to the female ramps 142 of the endplates 20, 22.

The distal end 166 of the front ramp 24 may define one or more horizontal ramps 170 configured to engage with the horizontal ramps 70 of the front plate 32. The front ramp 32 may define a pair of top and bottom horizontal ramps 170 separated by a gap and pointing inwardly toward one another. The horizontal ramps 170 may have an angled, diagonal, or slanted surface in a manner complimentary to the ramps 70 of the front plate 32. In particular, the horizontal ramps 170 may define male projections configured to enter the female counterparts 70 of the front plate 32. Similar to ramps 154, the ramps 170 may define a limiter 176 to end movement of the mating slides or ramps 70, 170. For example, the limiter 176 may include a widened ramp surface, a projection or protrusion, a bevel or dovetail, etc. configured to reduce or limit the relative movement between the ramps 70, 170.

Figure 10A:
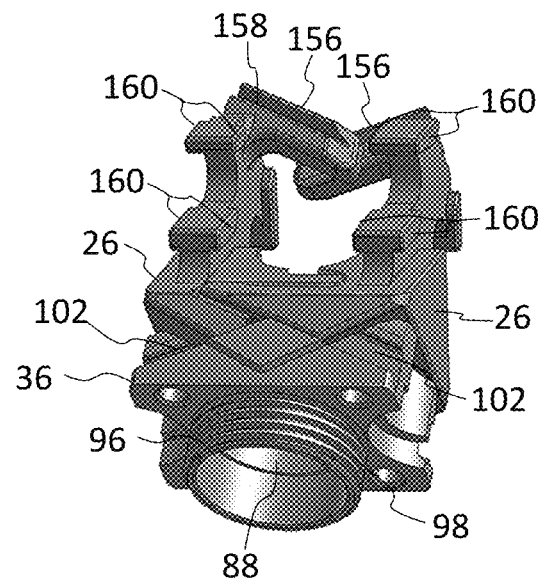
FIGS. 10A-10C illustrate the side actuators slidably engaged with the rear plate in a collapsed position and expanded in width, respectively, and a close-up view of the interaction between the side actuator and the rear plate according to one embodiment.
Figure 10B:
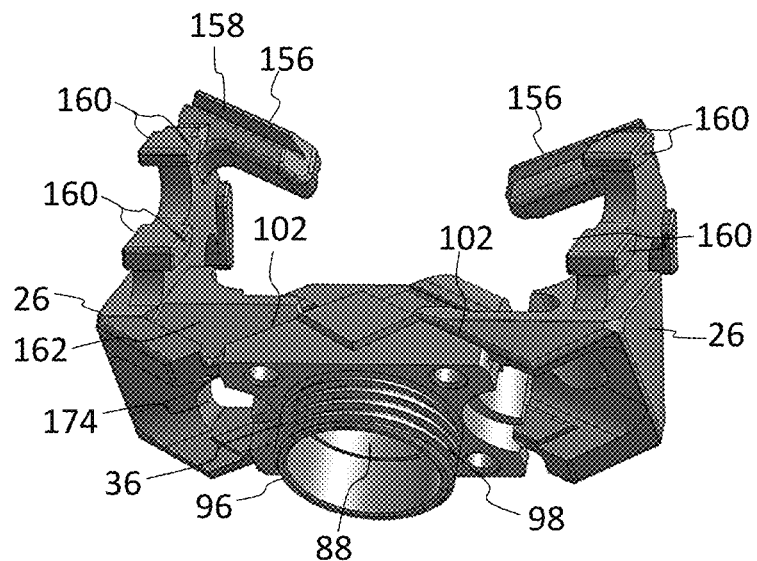
Figure 10C:
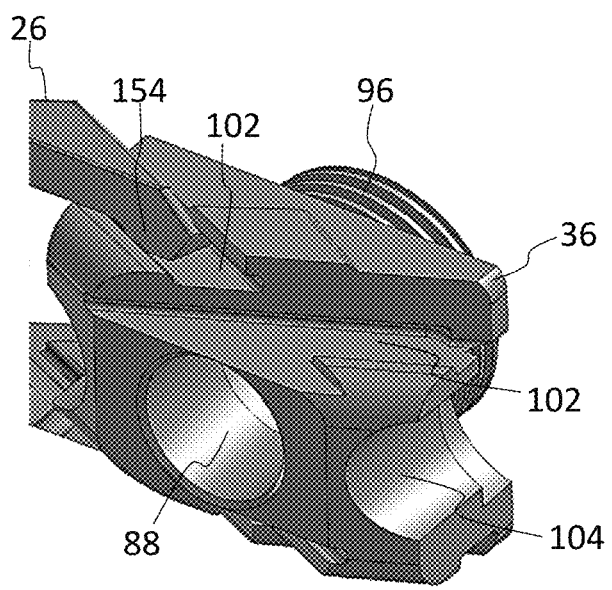

FIGS. 10A-10C show the side actuators 26 slidably engaged with the rear plate 36 in collapsed and expanded positions, respectively. The side actuators 26 slide onto the rear plate 36 by aligning keying features that control expansion. In FIG. 10A, the actuators 26 are engaged with the rear plate 36 and collapsed onto one another. A recessed surface 162 on top of the actuator 26 sized and dimensioned to receive the other actuator 26 permits the actuators 26 to nest together, thereby providing a small footprint for insertion. It will be appreciated that a corresponding recessed surface 162 may be provided on the bottom of the opposite actuator 26 to provide for a complimentary fit. As best seen in FIG. 10C, one horizontal ramp 102 is positioned deeper than another horizontal ramp 102 to further facilitate this nesting configuration of the adjacent side actuators 26. The horizontal male ramps 154 of the side actuators 26 slidably interface with the horizontal female ramps 102 of the rear plate 36, thereby permitting lateral or horizontal movement of the left and right side assemblies 12, 14. The side actuators 26 may have features that engage with the mating rear plate 36, such as limiters 176, that limit the amount of translation while expanding in width. When expanded laterally in width, the side actuators 26 slide outward and away from one another, thereby increasing the width of the implant 10. FIG. 10B shows the side actuators 26 fully expanded in width relative to the rear plate 32.

Figure 11A:
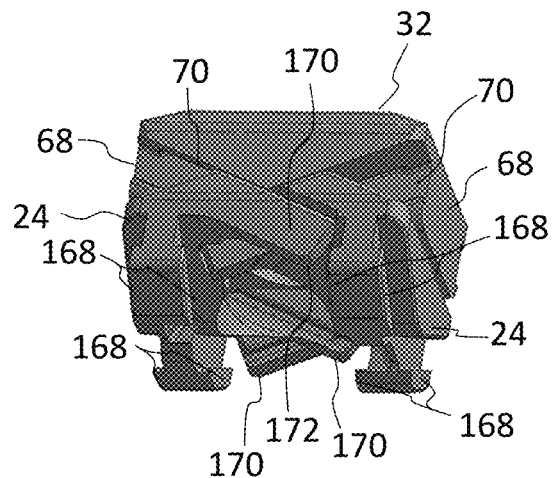
FIGS. 11A-11B illustrate the front ramps slidably engaged with the front plate in a collapsed position and expanded in width, respectively, according to one embodiment.
Figure 11B:
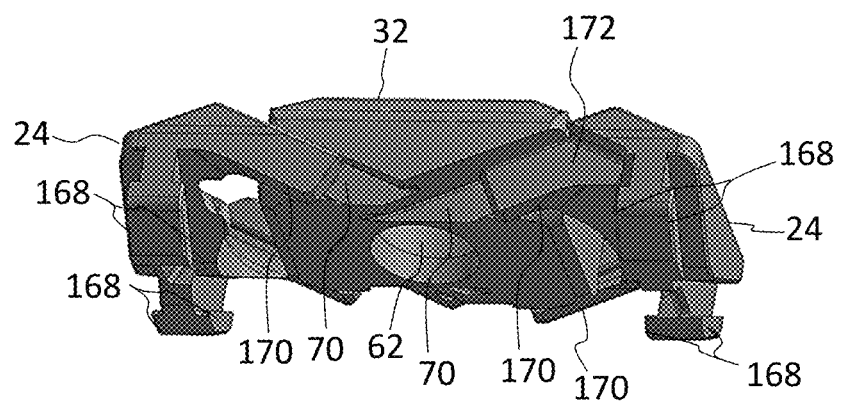

Front ramps 24 and front plate 32 utilize a similar sliding interface as actuators side 26 and rear plate 36. FIGS. 11A-11B show the front ramps 24 slidably engaged with the front plate 32 in collapsed and expanded positions, respectively. Front ramps 24 slide onto the front plate 32 by aligning keying features that control expansion. In FIG. 11A, the front ramps 24 are engaged with the front plate 32 and collapsed onto one another. A recessed surface 172 on top of one front ramp 24 sized and dimensioned to receive the other front ramp 24 permits the front ramps 24 to nest together, thereby providing a small footprint for insertion. It will be appreciated that a corresponding recessed surface 172 may be provided on the bottom of the opposite front ramp 24 to provide for a complimentary fit. Similar to rear plate 36, one horizontal ramp 70 may be positioned at a depth greater than the other horizontal ramp 70 to further facilitate this nesting configuration of the front ramps 24. The horizontal ramps 170 of the front ramps 24 slidably interface with the horizontal ramps 70 of the front plate 32. The front ramps 24 may also have features that engage with the mating front plate 32, such as limiters 176, that limit the amount of translation while expanding in width. In FIG. 11B, the front ramps 24 are fully expanded in width. When expanded in width, the front ramps 24 slide outward and away from one another, thereby increasing the overall width of the implant 10.

Figure 12A:
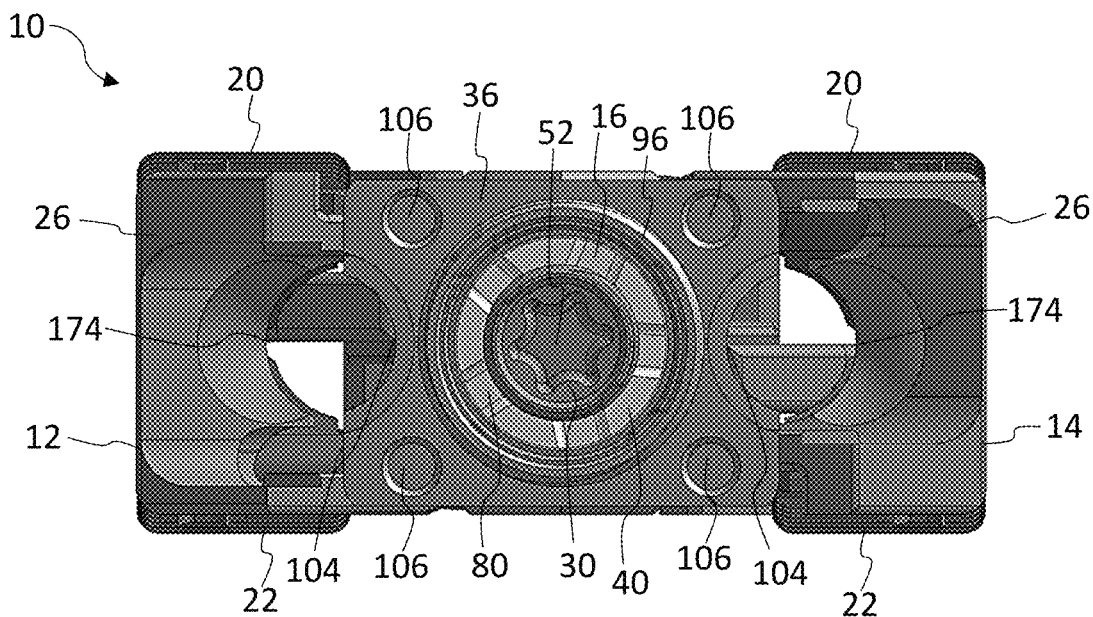
FIGS. 12A-12B show rear and perspective views, respectively, of the implant expanded in width according to one embodiment.
Figure 12B:
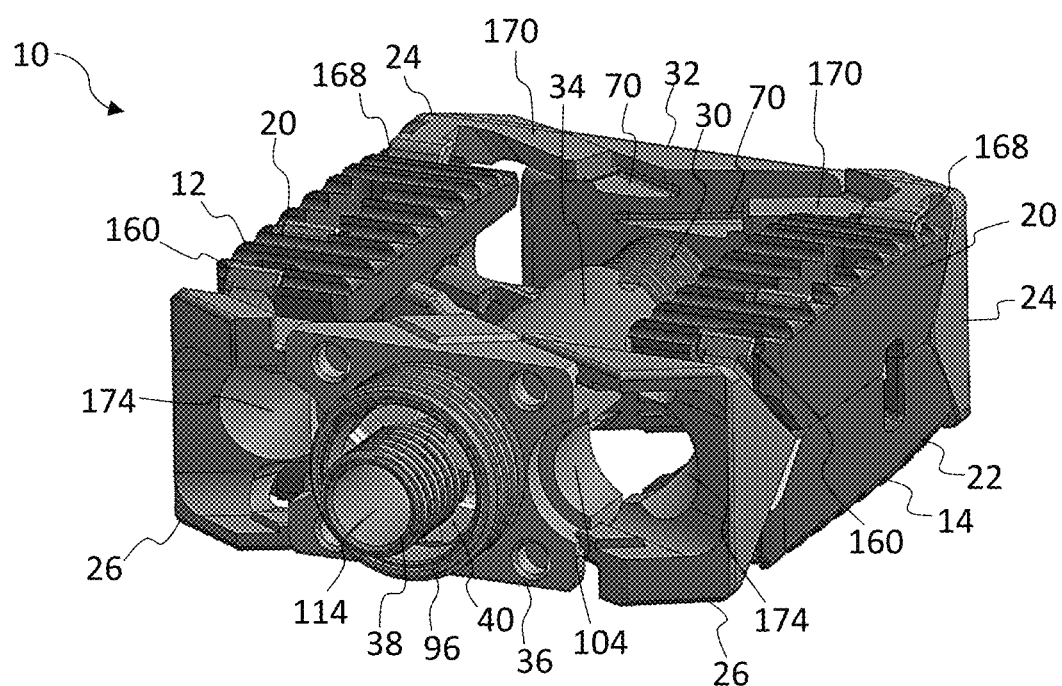

FIGS. 12A-12B show rear and perspective views, respectively, of the assembled implant 10 when fully expanded in width. The user is able to access the central drive assembly 16 through bore 88 in the rear plate 36. In particular, the drive nut 40 and drive screw 30 may be independently rotated or turned to actuate the implant 10. When the drive nut 40 is actuated, the threaded sleeve 38 is drawn proximally and the left and right side portions 12, 14 expand in width. Once expanded in width, the rear plate 36, which defines recesses 104, aligns with corresponding recesses 174 on the side actuators 28 to allow for access to a central portion of the implant 10. In this manner, a graft delivery device may be used to enter a central open area inside the implant 10 and deliver graft material therein. When the drive screw 30 is actuated, the left and ride side portions 12, 14 expand in height.

Figure 13A:
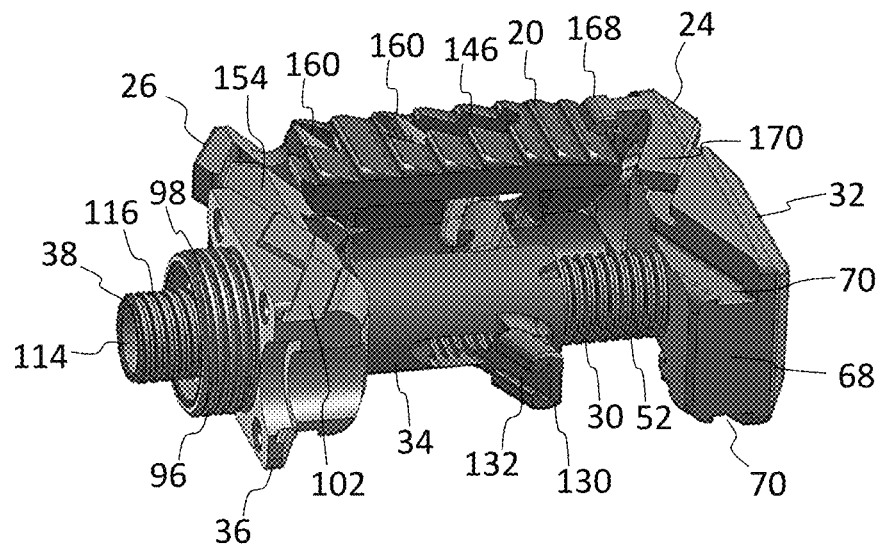
FIGS. 13A-13B show the implant fully expanded in width and fully expanded in width and height, respectively, according to one embodiment (one side assembly including one set of endplates, side actuator, and front ramp are omitted for clarity)
Figure 13B:
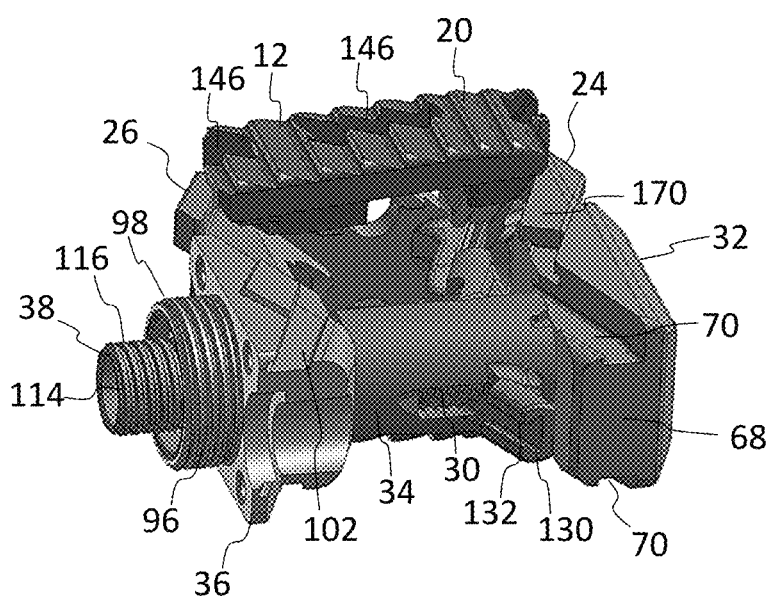

FIGS. 13A-13B show the implant 10 with the left side assembly 12 (one set of endplates 20, 22, side actuator 26, and front ramp 24 and hidden for clarity). The implant 10 may be fully collapsed to be inserted into a disc space, for example, through a posterior approach. The implant 10 may be attached to a multi-component instrument, for example. A first width driving instrument may be used to engage the recess 80 in the drive nut 40 with compatible drive features. When the drive nut 40 is rotated, it pulls or translates the threaded sleeve 38, central actuator 34, and front plate 32 proximally. When doing so, the drive nut 40 forces the side actuators 26 and front ramps 24 to translate outward and expand in width. Once the central actuator 34 and rear plate 36 come in contact with each other the drive nut 40 cannot be turned any further. As shown in FIG. 13A, full width expansion has been achieved. A second height driving instrument may be used to engage the recess 52 in the drive screw 30 with compatible drive features. When the drive screw 30 is rotated, the drive screw 30 pulls or translates the front plate 32 and front ramps 24 proximally. When doing so, the front ramps 24 translate proximally toward the side actuators 26 and force the endplates 20, 22 to translate upward and downward from the axial plane. Once the front plate 32 and the central actuator 34 come in contact with each other the drive screw 30 cannot be turned any further. As shown in FIG. 13B, the implant 10 is fully expanded in width and in height. The amount of height expansion on the left and right side assemblies 12, 14 may be the same or different. In this manner, the implant 10 is expanded in width for an increased footprint to aid in overall stability and the implant 10 is adjusted in lordosis and height for a precise patient fit.

The implant 10 may have a dual-sided or single-sided width expansion. In one embodiment, the expandable fusion device or implant 10 may be configured such that only one side assembly 12, 14 expands in width and the other remains stationary. Both of the left and right side portions 12, 14 may expand in height. In this embodiment, the front and rear plates 32, 36 may include only a single horizontal ramp on each of the top and bottom faces to engage with a single side actuator 26 and front ramp 24, respectively. The single side that does not expand laterally outward may incorporate the front ramp features into the front distal plate 32 and the actuator features into the rear proximal plate 36.

The implant 10 may be assembled as follows. The two front ramps 24 are placed onto the front plate 32 by aligning the slides or ramps 70, 170. One side actuator 26 is placed onto rear plate 36 by aligning the slides or ramps 102, 154. The central actuator 34 is placed onto the side actuator 26. The other side actuator 26 is placed onto the rear plate 36 and central actuator 34 by aligning slides or ramps 132, 156. The left and right sides 12, 14 may each be assembled by placing the lower endplate 22 onto the side actuator 26 and placing the upper endplate 20 onto side actuator 26. The front ramp 24 is placed into both the lower and upper endplates 20, 22. The threaded sleeve 38 is inserted into through the rear plate 36 and into central actuator 34 and secured. A friction ring 84 may be placed onto the drive nut 40. The drive nut 40 is then threaded on threaded sleeve 38 and bottomed out. The retaining sleeve 74 is pressed into rear plate 36, thereby securing drive nut 40. A friction ring 56 may be placed onto drive screw 30. Drive screw 30 is inserted through front plate 32 and threaded into central actuator 34. Retaining ring 58 may be placed into front plate 32, thereby securing drive screw 30.

Figure 14:
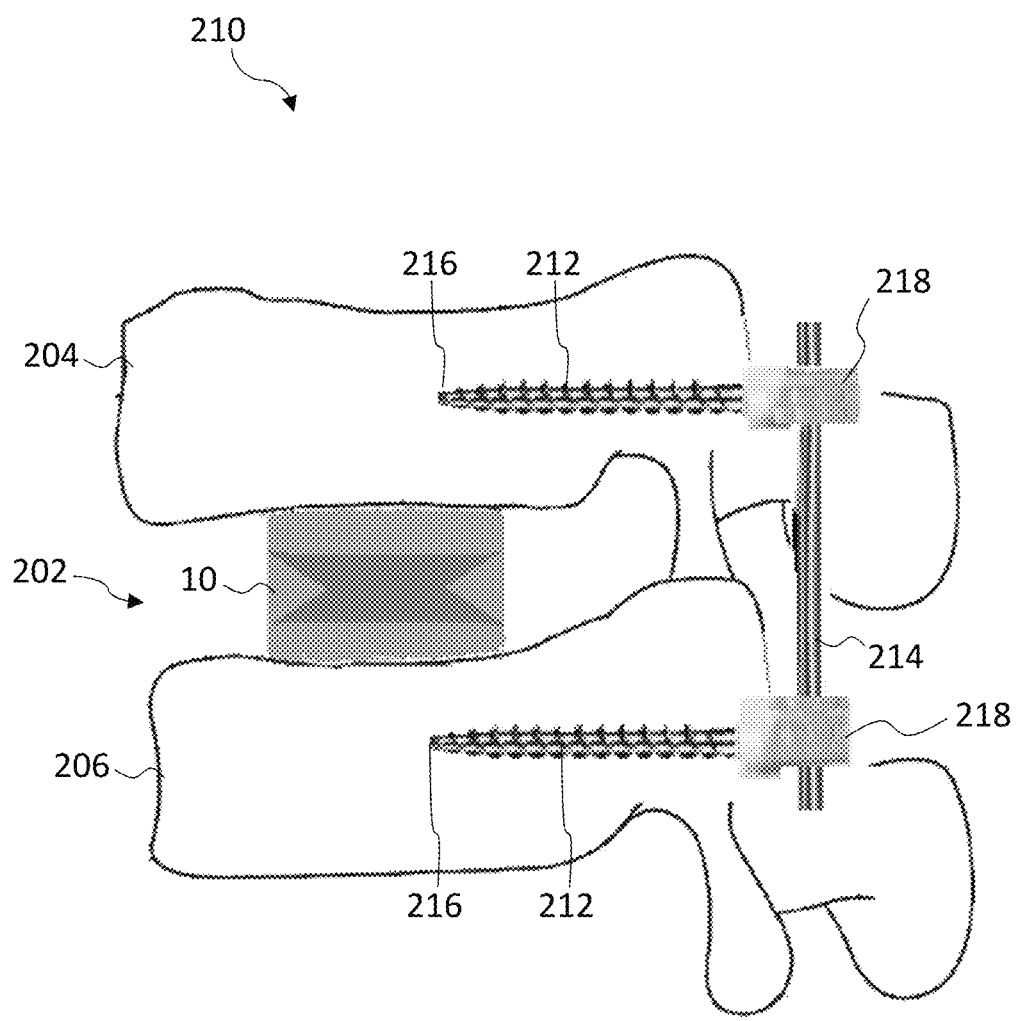
FIG. 14 illustrates a spinal construct including the expandable implant in combination with pedicle screws and attached spinal rod for stabilizing the posterior spine according to one embodiment.

Turning now to FIG. 14, a system 210 for intervertebral fusion is shown according to one embodiment. The system 210 may include expandable implant 10, a plurality of bone fasteners 212, and a spinal rod 214 connecting the bone fasteners 212. The expandable fusion device 10 may be surgically implanted into an intervertebral disc space 202 situated between upper and lower vertebrae 204, 206. A posterior aspect of the spine may be accessed, for example, through a minimally invasive surgical procedure. In one embodiment, the implant 10 may be implanted using a transforaminal lumbar interbody fusion (TLIF) procedure where a facet joint may be removed to access the disc space 202. The intervertebral disc or a portion thereof may be removed. The TLIF procedure may include a unilateral facetectomy to allow for visualization and removal of the disc. The implant 10 may be positioned in between the vertebrae 204, 206 to fuse the spine segment.

The disc level or levels may be further stabilized by inserting bone fasteners 212, such as pedicle screws, into the vertebrae 204, 206 above and below the implant 10, and connecting a spinal rod 214 to the fasteners 212. The bone fasteners 212 may include bone screws, anchors, clamps, or the like configured to engage bone. In the embodiment shown, the bone fastener 212 is a bone screw, which extends from a proximal end to a distal tip 216. The proximal end may include an enlarged head receivable within a modular tulip element 218, such as a polyaxial bone screw. The tulip head 218 is configured to secure spinal rod 214. Examples of bone fasteners and other implants and rod constructs are described in more detail, for example, in U.S. Pat. No. 10,368,917, which is incorporated by reference herein in its entirety for all purposes. The pedicle screws 212 may be used with a spinal fusion to add extra support and strength to the fusion while it heals. The pedicle screws 212 may be placed above and below the vertebrae 204, 206 to be fused. Although only a single rod 214 is shown, a bilateral construct may be used with a pair of rods 214 secured laterally along each side of the spine.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all components of the various devices disclosed above may be combined or modified in any suitable configuration.

What is claimed is:

1. A spinal fixation system comprising:
an expandable intervertebral implant comprising a central drive assembly aligned along a central longitudinal axis of the implant and left and right side assemblies defining opposing lateral sides of the implant,
the central drive assembly including a front plate at a distal end of the implant, an externally threaded central drive screw, a central actuator having a tubular body with a through bore comprising inner threads and a pair of opposed wings, an externally threaded sleeve, a rear plate, and a drive nut at a proximal end of the implant, wherein the central drive screw is retained in the front plate and is threadedly engaged with the inner threads of the tubular body of the central actuator, the central actuator is threadedly engaged with the externally threaded sleeve, and the externally threaded sleeve is retained in the rear plate and threadedly engaged with the drive nut, and the left and right side assemblies each including upper and lower endplates, a side actuator, and a front ramp,
wherein the pair of opposed wings each define a female ramp configured to receive a corresponding male ramp from each side actuator,
wherein the rear plate includes a pair of female horizontal ramps defined into top and bottom surfaces of the rear plate, and each side actuator includes a pair of horizontal male ramps configured to interface with the respective female horizontal ramps of the rear plate;
wherein the front plate includes a pair of female horizontal ramps defined into top and bottom surfaces of the front plate, and each front ramp includes a pair of male horizontal ramps configured to interface with the respective female horizontal ramps of the front plate,
wherein the left and right side assemblies have a laterally collapsed configuration having a first width and a laterally expanded configuration having a second width larger than the first width, and wherein the left and right side assemblies have a vertically collapsed configuration having a first height and a vertically expanded configuration having a second height larger than the first height, and
wherein the drive nut and the central drive screw are independently rotatable such that rotation of the drive nut is configured to expand the implant in width and rotation of the central drive screw is configured to expand the implant in height;
at least one bone fastener; and
at least one spinal rod attachable to the at least one bone fastener.

2. The spinal fixation system of claim 1, wherein the expandable intervertebral implant is configured to be installed through a transforaminal lumbar interbody fusion procedure.

3. The spinal fixation system of claim 1, wherein the at least one bone fastener includes a threaded shaft and a tulip head.

4. The spinal fixation system of claim 1, wherein the at least one bone fastener is a polyaxial bone screw.

5. The spinal fixation system of claim 1, wherein the at least one bone fastener is a pedicle screw.

6. The spinal fixation system of claim 1, wherein the at least one bone fastener comprises a plurality of bone fasteners configured to be installed in vertebrae adjacent to the expandable intervertebral implant.

7. The spinal fixation system of claim 1, wherein the at least one bone fastener includes a set of bone fasteners and the at least one spinal rod comprises a set of spinal rods configured to stabilize the spine.

8. A spinal fixation system comprising:
an expandable intervertebral implant comprising a central drive assembly aligned along a central longitudinal axis of the implant and left and right side assemblies defining opposing lateral sides of the implant,
the central drive assembly including a front plate at a distal end of the implant having a central through bore, an externally threaded central drive screw having an enlarged head and a threaded shaft positioned through the through bore in the front plate, a central actuator having a tubular body with a through bore and a pair of opposed wings, the threaded shaft of the central drive screw threadedly engaged within one end of the bore of the central actuator, a rear plate having a central through bore, an externally threaded sleeve positioned through the bore in the rear plate and threadedly engaged with an opposite end of the bore of the central actuator, a drive nut at a proximal end of the implant threadedly engaged with the threaded sleeve, and
the left and right side assemblies each including upper and lower endplates, a side actuator, and a front ramp,
wherein the pair of opposed wings each define a female ramp configured to receive a corresponding male ramp from each side actuator,
wherein the rear plate includes a pair of female horizontal ramps defined into top and bottom surfaces of the rear plate, and each side actuator includes a pair of horizontal male ramps configured to interface with the respective female horizontal ramps of the rear plate;
wherein the front plate includes a pair of female horizontal ramps defined into top and bottom surfaces of the front plate, and each front ramp includes a pair of male horizontal ramps configured to interface with the respective female horizontal ramps of the front plate,
wherein the left and right side assemblies have a laterally collapsed configuration having a first width and a laterally expanded configuration having a second width larger than the first width, and wherein the left and right side assemblies have a vertically collapsed configuration having a first height and a vertically expanded configuration having a second height larger than the first height,
wherein the drive nut and the central drive screw are independently rotatable such that rotation of the drive nut is configured to expand the implant in width and rotation of the central drive screw is configured to expand the implant in height; and
a posterior stabilization system comprising a plurality of bone fasteners including a threaded shaft and a tulip head, and at least one spinal rod affixed to the tulip heads of the bone fasteners to stabilize a portion of the spine.

9. The spinal fixation system of claim 8, wherein the plurality of bone fasteners are configured to be inserted into pedicles of adjacent vertebrae.

10. The spinal fixation system of claim 8, wherein independent rotation of the drive nut is configured to expand the intervertebral implant in width.

11. The spinal fixation system of claim 8, wherein independent rotation of the central drive screw is configured to expand the intervertebral implant in height in-situ.

12. A method of spinal fixation comprising:
inserting the expandable intervertebral implant recited in claim 1 into a disc space;
expanding the expandable intervertebral implant in width and/or height;
affixing a plurality of bone screws to pedicles of adjacent vertebrae; and
connecting at least one spinal rod between the bone screws.

13. The method of claim 12, wherein expanding the implant in width includes independently rotating the drive nut and expanding the implant in height includes independently rotating the central drive screw.

14. The method of claim 12, further comprising, before inserting the expandable intervertebral implant into the disc space, accessing a posterior aspect of a spine, and performing a facetectomy.

15. The method of claim 12, further comprising performing a unilateral facetectomy to allow for visualization and removal of a disc.

16. The method of claim 12, wherein the expandable intervertebral implant is expanded in width to increase an overall footprint size, thereby minimizing a potential for implant subsidence.

17. The method of claim 12, wherein the expandable intervertebral implant is expanded in height in-situ to adjust lordosis.

18. The method of claim 12, wherein the step of affixing a plurality of bone screws comprises affixing a first set of bone screws is affixed and a second set of bone screws to pedicles of the adjacent vertebrae, and wherein the step of connecting at least one spinal rod comprises connecting a first spinal rod therebetween the first set of bone screws and connecting a second spinal rod is connected therebetween the second set of bone screws.

\* \* \* \* \*